(12) United States Patent
Perregaard et al.

(10) Patent No.: US 6,352,988 B2
(45) Date of Patent: Mar. 5, 2002

(54) INDANE OR DIHYDROINDOLE DERIVATIVES

(75) Inventors: Jens Kristian Perregaard, Jaegerspris; Benny Bang-Andersen, Copenhagen N; Henrik Pedersen, Bronshoj; Ivan Mikkelsen, Koge; Robert Dancer, Frederiksberg, all of (DK)

(73) Assignee: H. Lundbeck A/S, Valby-Copenhage (DK)

( * ) Notice: Subject to any disclaimer, the term of this patent is extended or adjusted under 35 U.S.C. 154(b) by 0 days.

(21) Appl. No.: 09/814,037

(22) Filed: Mar. 21, 2001

Related U.S. Application Data

(62) Division of application No. 09/331,560, filed as application No. PCT/DK97/00587 on Dec. 19, 1997, now Pat. No. 6,262,087.

(30) Foreign Application Priority Data

Dec. 20, 1996 (DK) ................................. 1514/96

(51) Int. Cl.[7] .................... A61K 31/496; C07D 403/14; C07D 403/04
(52) U.S. Cl. .................... 514/254; 544/373; 514/255
(58) Field of Search ................. 514/254, 255; 544/373

(56) References Cited

U.S. PATENT DOCUMENTS 4,933,453 A    6/1990   Hrib et al. ................... 544/297
5,693,655 A   12/1997   Bottcher et al. ............ 514/323

FOREIGN PATENT DOCUMENTS

| DE | 44 14 113 | 10/1995 | ......... C07D/401/04 |
| WO | WO 94/21627 | 9/1994 | ......... C07D/401/06 |
| WO | WO 95/33721 | 12/1995 | ......... C07D/211/18 |
| WO | WO 99/67237 | 12/1999 | ......... C07D/405/14 |

OTHER PUBLICATIONS

Norman et al., "Synthesis and Evaluation of Heterocyclic Carboxamides as Potential Antipsychotic Agents," *J. Med. Chem.* 39, 24:4692–4703 (1996).

*Primary Examiner*—Charanjit S. Aulakh
(74) *Attorney, Agent, or Firm*—Darby & Darby

(57) ABSTRACT

The present invention relates to substituted indane or dihydroindole compounds of Formula (I)

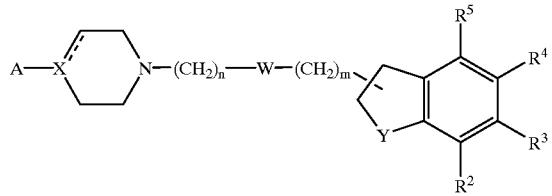

wherein A is an indole. These compounds have high affinity for $D_4$ receptors.

59 Claims, No Drawings

INDANE OR DIHYDROINDOLE DERIVATIVES

This Application is a Div. of Ser. No. 09/331,560 filed Jun. 21, 1999, U.S. Pat. No. 6,262,087, which is a 371 of PCT/DK97/00587 filed Dec. 19, 1997.

FIELD OF THE INVENTION

The present invention relates to a novel class of substituted indane or dihydroindole compounds having effect at dopamine $D_4$ receptors. The compounds are selective dopamine $D_4$ ligands or they have combined effects at dopamine $D_4$, 5-HT receptors and/or the 5-HT transporter. These compounds are therefore useful in the treatment of certain psychiatric and neurologic disorders, including psychosis, depression and anxiety.

BACKGROUND OF THE INVENTION

Compounds related to the compounds of the present invention are known from DE patent application No. 4414113 describing certain 4-(indol-3-yl)-1-(indol-3-yl-alkylene)-piperidines. The compounds herein are claimed to show serotonin antagonistic and agonistic activities and to have effect on DOPA-accumulation in striatum. No biological data are given.

GB patent application No. 2 044 254 describes certain 1-(indol-3-yl-alkylene)-piperidine derivatives which are substituted in position 3 or 4 of the piperidine ring with an isoindole, or an isoquinoline ring. These compounds are claimed to have 5-HT reuptake inhibiting activity and to be useful as antidepressants.

Furthermore, in WO patent publications No. WO 9421627, WO 9421630 and WO 94 21626 various series of indolyl- or indazolylmethyl piperidine or piperazine derivatives are described to be selective dopamine $D_4$ antagonists. No data are given. The compounds are only said to give $K_i$ values of less than 1.5 $\mu$M in a test for displacement of $^3$H spiperone from human dopamine $D_4$ receptor subtypes in clonal cell lines.

WO patent publication No. 95/33721 relates to 1-(indanemethyl, dihydrobenzofuranylmethyl, or dihydrobenzothiophenylmethyl)piperidine, -tetrahydropyridine, or piperazine derivatives. The 1-indanemethyl compounds disclosed herein are substituted in position 6 with an amino containing group. The compounds interact with central 5-HT receptors, in particular with 5-$HT_{1A}$ and 5-$HT_{2A}$ receptors. Some of the compounds are said to have 5-HT reuptake inhibiting effect.

Dopamine $D_4$ receptors belong to the dopamine $D_2$ receptor family which is considered to be responsible for the antipsychotic effects of neuroleptics. Dopamine $D_4$ receptors are primarily located in areas of the brain other than striatum (Van Tol, et al. Nature, 1991, 350, 610). The low level of $D_4$ receptors in striatum suggesting that compounds which are selective for the dopamine $D_4$ receptor will be devoid of extrapyramidal activity, is illustrated by the antipsychotic clozapine which has a high affinity for dopamine $D_4$ receptors and is lacking extrapyramidal side effects, (Van Tol, et al. Nature, 1991, 350, 610). Also, dopamine $D_4$ receptor levels have been reported to be elevated in schizophrenic patients (Seeman et al., Nature, 1993, 365, 441.).

Various effects are known with respect to compounds which are ligands at the different serotonin receptor subtypes. As regards the 5-$HT_{2A}$ receptor, which was previously referred to as the 5-$HT_2$ receptor, the following effects have e.g. been reported:

Antidepressive effect and improvement of the sleep quality (Meert, T. F.; Janssen, P. A. 3. Drug. Dev. Res. 1989, 18, 119.) reduction of the negative symptoms of schizophrenia and of extrapyramidal side-effects caused by treatment with classical neuroleptics in schizophrenic patients (Gelders, Y. G., British J. Psychiatry, 1989, 155 (suppl. 5, 33). Finally, selective 5-$HT_{2A}$ antagonists could be effective in the prophylaxis and treatment of migraine (Scrip Report; "Migraine—Current trends in research and treatment"; PJB Publications Ltd.; May 1991).

Clinical studies have shown that 5-$HT_{1A}$ partial agonists are useful in the treatment of anxiety disorders such as generalised anxiety disorder, panic disorder, and obsessive compulsive disorder (Glitz, D. A., Pohl, R., Drugs 1991, 41, 11). Preclinical studies indicate that full agonists are useful in the treatment of the above mentioned anxiety related disorders (Schipper, Human Psychopharmacol., 1991, 6, S53).

There is evidence, both clinical and preclinical, in support of the beneficial effect of 5-$HT_{1A}$ partial agonists in the treatment of depression, impulse control disorders and alcohol abuse (van Hest, Psychopharmacol., 1992, 107, 474; Schipper et al, Human Psychopharmacol., 1991, 6, S53; Cervo et al, Eur. J. Pharm., 1988, 158, 53; Glitz and Poh, Drugs 1991, 41, 11; Grof et al., Int. Clin. Psychopharmacol. 1993, 8, 167–172; Ansseau et al., Human Psychopharmacol. 1993, 8, 279–283).

5-$HT_{1A}$ agonists and partial agonists inhibit isolation-induced aggression in male mice indicating that these compounds may be useful in the treatment of aggression (Sanchéz et al., Psychopharmacology, 1993, 110, 53–59).

Furthermore, 5-$HT_{1A}$ ligands have been reported to show antipsychotic effect in animal models (Wadenberg and Ahlenius, J. Neural. Transm., 1991, 83, 43; Ahlenius, Pharmacol. & Toxicol., 1989, 64, 3; Lowe et al., J. Med. Chem., 1991, 34, 1860; New et al., J. Med. Chem., 1989, 32, 1147; and Martin et al., J. Med. Chem., 1989, 32, 1052).

Recent studies also indicate that 5-$HT_{1A}$ receptors are important in the serotonergic modulation of haloperidol-induced catalepsy (Hicks, Life Science 1990, 47, 1609, Wadenberg et al. Pharmacol.Biochem. & Behav. 1994, 47, 509–513) suggesting that 5-$HT_{1A}$ agonists are useful in the treatment of extrapyramidal side-effects induced by conventional antipsychotic agents such as haloperidol.

5-$HT_{1A}$ agonists have shown neuroprotective properties in rodent models of focal and global cerebral ischaemia and may, therefore, be useful in the treatment of ischaemic disease states (Prehn, Eur. J. Pharm. 1991, 203, 213).

Pharmacological studies have been presented which indicate that 5-$HT_{1A}$ antagonists are useful in the treatment of senile dementia (Bowen et al, Trends Neur. Sci. 1992, 15, 84). 5-HT reuptake inhibitors are well known antidepressant drugs.

Accordingly, dopamine $D_4$ receptor ligands are potential drugs for the treatment of psychoses and positive symptoms of schizophrenia and compounds with combined effects at dopamine $D_4$ and 5-HT receptors and/or the 5-HT transporter may have the further benefit of improved effect on other psychiatric symptoms in schizophrenic patients such as depressive and anxiety symptoms. 5-$HT_{1A}$ and 5-$HT_{2A}$ receptor ligands and 5-HT reuptake inhibitors have different activities in different animal models predictive of anxiolytic and antiaggressive effects (Perregaard et al., Recent Developments in Anxiolytics. Current Opinion in Therapeutic Patents 1993, 1, 101–128) and/or in models predictive of effects in other psychic disorders and it is considered highly beneficial to have such combined serotonergic effects.

Compounds with dopamine $D_4$ receptor activity combined with effect at 5-HT receptors and compounds with dopamine $D_4$ receptor activity combined with 5-HT reuptake inhibiting effect is considered a new therapeutic approach in the treatment of neurologic and psychiatric disorders, including in particular psychosis.

SUMMARY OF THE INVENTION

The object of the present invention is to provide compounds with dopamine $D_4$ activities or with combined effects at dopamine $D_4$ receptors, 5-HT receptors and/or the 5-HT transporter.

It has now been found that certain substituted indane or dihydroindole compounds have effect at dopamine $D_4$ receptors. Additionally, many of the compounds interact with central serotonergic receptors, in particular with the $5\text{-HT}_{1A}$ and/or the $5\text{-HT}_{2A}$ receptors and/or they act as 5-HT reuptake inhibitors.

Accordingly, the present invention relates to novel compounds of the formula I

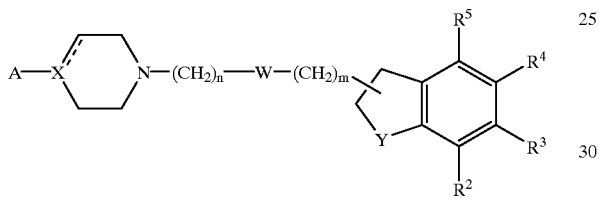

wherein A is a group a)

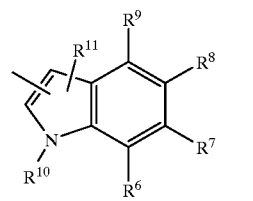

b)

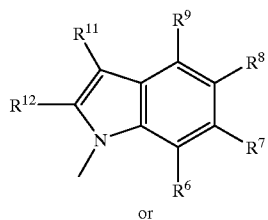

or c)

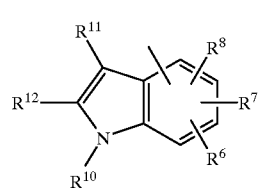

Y is a hydrocarbon group completing an indane ring, a group $NR^1$ completing a dihydroindole ring, or a group N completing a dihydroindole ring linked via the 1-position;

W is a bond, and n+m is 1, 2, 3, 4, 5, or 6;
W is CO, SO, or $SO_2$, n is 2, 3, 4, or 5 and m is 0, 1, 2, or 3, provided that n+m is not more than 6; or
W is O, S, n is 2, 3, 4, or 5 and m is 0, 1, 2, or 3, provided that n+m is not more than 6, and
if Y is N completing a dihydroindole ring attached via the 1-position then m is 2, or 3; and
if Y is $NR^1$ completing a dihydroindole ring linked via the 2-position then m is 1, 2, or 3; the dotted line, emanating from X, indicates an optional bond; when it does not indicate a bond, X is N, CH or COH; and when it indicates a bond, X is C;

$R^1$ is
hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, aryl, heteroaryl, aryl-$C_{1-6}$ alkyl, heteroaryl-$C_{1-6}$-alkyl, acyl, thioacyl, $C_{1-6}$-alkylsulfonyl, trifluoromethylsulfonyl, arylsulfonyl, or heteroarylsulfonyl
$R^{15}VCO$— wherein V is O or S and $R^{15}$ is $C_{1-6}$-alk(en/yn)yl, $C_{3-8}$-cycloalk(en)yl, $C_{3-8}$-cycloalk(en)yl-$C_{1-6}$-alk(en/yn)yl, aryl, or heteroaryl; or
a group $R^{16}R^{27}NCO$— or $R^{16}R^{17}NCS$- wherein $R^{16}$ and $R^{17}$ are independently hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, heteroaryl, or aryl, or $R^{16}$ and $R^{17}$ together with the N-atom to which they are linked, form a pyrrolidinyl, piperidinyl or perhydroazepin group;

$R^2$–$R^5$ are independently selected from hydrogen, halogen, cyano, nitro, $C_{1-6}$-alk(en/yn)yl, $C_{1-6}$ alkoxy, $C_{1-6}$-alkylthio, hydroxy, $C_{3-8}$-cycloalk(en)yl, $C_{3-8}$-cycloalk(en)yl-$C_{1-6}$-alk(en/yn)yl. $C_{1-6}$-alkylcarbonyl, phenylcarbonyl, halogen substituted phenylcarbonyl, trifluoromethyl, trifluoromethylsulfonyloxy and $C_{1-6}$ alkylsulfonyl, one of $R^2$–$R^5$ alternatively being a group —$NR^{13}R^{14}$ wherein $R^{13}$ is as defined for $R^1$ and $R^{14}$ is hydrogen, $C_{1-6}$-alk(en/yn)yl, $C_{3-8}$-cycloalk(en)yl, $C_{3-8}$-cycloalk(en)yl-$C_{1-6}$ alk(en/yn)yl, aryl, heteroaryl, aryl-$C_{1-6}$ alkyl, or heteroaryl-$C_{1-6}$-alkyl, or $R^{13}$ and $R^{14}$ together with the N-atom to which they are linked form a group

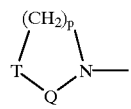

wherein
Q is C=O, C=S or $CH_2$; T is NH, N-alkyl, S, O or $CH_2$; and p is 1–4, inclusive; or two adjacent groups taken from $R^2$–$R^5$ may be joined and designate —$(CH_2)_3$—, or —CH=CH—NH—, thereby forming a fused 5 membered ring;

$R^6$–$R^9$ and $R^{11}$–$R^{12}$ are independently hydrogen, halogen, cyano, nitro, $C_{1-6}$-alk(en/yn)yl. $C_{1-6}$-alkoxy, $C_{1-6}$-alkylthio, hydroxy, $C_{3-8}$-cycloalk(en)yl, $C_{3-8}$-cycloalk(en)yl-$C_{1-6}$ alk(en/yn)yl, aryl, heteroaryl, phenylcarbonyl, halogen substituted phenylcarbonyl, trifluoromethyl, or $C_{1-6}$ alkylsulfonyl or two adjacent groups taken from $R^6$–$R^9$ may together form a methylenedioxy group;

$R^{10}$ is as defined for $R^1$ above;
with the proviso that the substituent $R^3$ or $R^4$ in position 6 may not be —$N^{13}R^{14}$ when Y is $CH_2$, W is a bond, n+m is 1 and the ring is linked via the 1-position; or a pharmaceutically acceptable acid addition salt thereof.

The compounds of the invention have been found to show high affinity for dopamine $D_4$ receptors and some of the compounds have been found also to show affinity for serotonergic receptors including 5-$HT_{1A}$ receptors and/or for 5-$HT_{2A}$ receptors. An important group of compounds according to the invention are the compounds which have effect at dopamine $D_4$ receptors combined with 5-HT reuptake inhibiting effect.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders, aggression, side effects induced by conventional antipsychotic agents, ischaemic disease states, migraine, senile dementia and cardiovascular disorders and in the improvement of sleep.

In another aspect of the present invention provides a pharmaceutical composition comprising at least one compound of Formula I as defined above or a pharmaceutically acceptable acid addition salt thereof in a therapeutically effective amount and in combination with one or more pharmaceutically acceptable carriers or diluents.

In a further aspect the present invention provides the use of a compound of Formula I as defined above or an acid addition salt thereof for the manufacture of a pharmaceutical preparation for the treatment of the above mentioned disorders.

DETAILED DESCRIPTION OF THE INVENTION

Some of the compounds of general Formula I exist as optical isomers thereof and such optical isomers are also embraced by the invention.

The expression $C_{1-6}$-alk(en/yn)yl means $C_{1-6}$-alkyl, $C_{2-6}$-alkenyl, or $C_{2-6}$-alkynyl group.

The expression $C_{3-8}$-cycloalk(en)yl means a $C_{3-8}$-cycloalkyl group, or a $C_{3-8}$-cycloalkenyl group.

The term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and triple bond respectively, such as ethenyl, propenyl, butenyl, ethynyl, propynyl, and butynyl.

The terms $C_{1-6}$ alkoxy, $C_{1-6}$ alkylthio, $C_{1-6}$ alkylsulfonyl, $C_{1-6}$ alkylamino, $C_{1-6}$ alkylcarbonyl, etc. designate such groups in which the alkyl group is $C_{1-6}$ alkyl as defined above.

The term $C_{3-8}$ cycloalkyl designates a monocyclic or bicyclic carbocycle having three to eight C-atoms, such as cyclopropyl, cyclopentyl, cyclohexyl, etc.

The term $C_{3-8}$ cycloalkenyl designates a monocyclic or bicyclic carbocycle having three to eight C-atoms and containing one double bond.

The term aryl refers to a carbocyclic aromatic group, such as phenyl, naphthyl, in particular phenyl, including methyl substituted naphthyl, or phenyl.

The term heteroaryl refers to a mono- or bicyclic heterocyclic group such as indolyl, thienyl, pyrimidyl, oxazolyl, isoxazolyl, thiazolyl, isothiazolyl, imidazolyl, benzofuranyl, benzothienyl, pyridyl and furanyl, in particular pyrimidyl, indolyl, and thienyl.

Halogen means fluoro, chloro, bromo or iodo.

As used herein the term acyl refers to a formyl, $C_{1-6}$alk(en/yn)ylcarbonyl, arylcarbonyl, aryl-$C_{1-6}$alk(en/yn)ylcarbonyl, $C_{3-8}$-cycloalk(en)ylcarbonyl, or a $C_{3-8}$cycloalk(en)yl-$C_{1-6}$ alk(en/yn)ylcarbonyl group and the term thioacyl is the corresponding acyl group in which the carbonyl group is replaced with a thiocarbonyl group.

One group of compounds according to the invention are the compounds wherein Y is completing an indane ring.

Other groups of compounds according to the invention are the groups of compounds wherein Y is $NR^1$ or N completing a dihydroindole ring.

Accordingly, one group of compounds are the compounds wherein Y is $CH_2$ and A is a group a) linked to X via the 2 or the 3 position, or a group b), in particular a group a).

Another group of compounds are the compounds wherein Y is $CH_2$ and A is a group group c) linked to X via the 4, 5, 6, or 7 position.

A third and fourth group of compounds are the compounds wherein Y is NR or N and A is a group a) linked to X via the 2 or the 3 position, or a group b), in particular a group a).

A fifth and sixth group of compounds are the compounds wherein Y is $NR^1$ or N and A is a group c) linked to X via the 4, 5, 6, or 7 position.

Particular embodiments of the present invention are compounds wherein Y is a hydrocarbon group completing an indane ring and

- linked via the 2 position and A is a group a) which is linked via position 3;
- linked via the 2 position and A is a group a) which is linked via position 2;
- linked via the 2 position and A is a group b);
- linked via the 2 position A is a group c) which is linked via position 4, 5, 6, or 7;
- linked via the 1 position A is a group a) which is linked via position 3;
- linked via the 1 position and A is a group a) which is linked via position 2;
- linked via the 1 position A is a group b); or
- linked via the 1 position and A is a group c) which is linked via position 4, 5, 6, or 7.

Other particular embodiments of the present invention are compounds wherein Y is $NR^1$ completing dihydroindole ring which is

- linked via the 3 position and A is a group a) which is linked via position 3;
- linked via the 3 position and A is a group a) which is linked via position 2;
- linked via the 3 position and A is a group b);
- linked via the 3 position and A is a group c) which is linked via position 4, 3, 6, or 7,
- linked via the 2 position and A is a group a) which is linked via position 3,
- linked via the 2 position and A is a group a) which is linked via position 2,
- linked via the 2 position and A is a group b); or
- linked via the 2 position and A is a group c) which is linked via position 4, 5, 6, or 7.

Still other particular embodiments of the present invention are compounds wherein Y is N completing dihydroindole and A is a group a) which is linked via position 3;
A is a group a) which is linked via position 2;
A is a group b); or
A is a group c) which is linked via position 4, 5, 6, or 7.

In one group of compounds W is a bond, n+m is 1 to 4, or n+m is selected from 1 and/or 2. Other groups of compounds are compounds wherein W is a bond n+m is 2 to 6, 2 to 5, 2 to 4, 3 to 6, 3 to 5, or 3 to 4.

When W is not a bond it is O, or CO.

Three further group of compounds are the compounds wherein X is CH, X is C, and X is N respectively.

$R^1$ is in a particular embodiment selected from hydrogen, $C_{1-6}$-alkyl, formyl, $C_{1-6}$-alkylcarbonyl, $C_{1-6}$-alkoxycarbonyl or $C_{1-6}$-alkylaminocarbonyl.

In on embodiment of the invention $R^2$ to $R^5$ are independently selected from hydrogen, halogen, cyano, nitro, $C_{1-6}$-alkyl, $C_{1-6}$ alkoxy, $C_{1-6}$-alkylthio, hydroxy, $C_{3-8}$-cycloalkyl, $C_{3-8}$-cycloalkyl-$C_{1-6}$-alkyl, $C_{1-6}$-alkylcarbonyl, trifluoromethyl, trifluoromethylsulfonyloxy and $C_{1-6}$ alkylsulfonyl, one of $R^2$ to $R^5$ alternatively being a group —$NR^{13}R^{14}$ wherein $R^{13}$ is hydrogen, $C_{1-6}$-alkyl, acyl, $C_{1-6}$-alkylsulfonyl, or a group —$R^{16}R^{17}NCO$ wherein $R^{16}$ is hydrogen, $C_{1-6}$-alkyl, $C_{3-8}$-cycloalkyl, or $C_{3-8}$-cycloalkyl-$C_{1-6}$-alkyl, and $R^{17}$ is hydrogen or $C_{1-6}$-alkyl, or $R^{16}$ and $R^{17}$ together with the N-atom to which they are linked, form a pyrrolidinyl, piperidinyl, or perhydroazepin group and $R^{14}$ is hydrogen or $C_{1-6}$-alkyl, or $R^{13}$ and $R^{14}$ are linked together to form pyrrolidinyl, piperidinyl, perhydroazepin or a 5 to 7 membered unsubstituted lactam ring, in particular $R^2$ to $R^5$ is selected from hydrogen, halogen, cyano, nitro, $C_{1-6}$-alkyl, $C_{1-6}$-alkoxy, trifluoromethyl, and trifluoromethylsulfonyloxy.

In one group of compounds according to the invention none of of $R^2$–$R^5$ is a group $NR^{13}R_{14}$, and in another group of compounds according to the invention at )east one of $R^2$–$R^5$ is a group $NR^{13}$–$R^{14}$, wherein $R^{13}$ is preferably selected from methyl, formyl, acetyl, methylaminocarbonyl, dimethylaminocarbonyl, methylsulfonyl, aminocarbonyl, cyclopropylcarbonyl, pyrrolidinylcarbonyl or 4-fluorophenylaminocarbonyl and $R^{14}$ is preferably selected from hydrogen or $C_{1-6}$-alkyl.

Another particular group of compounds according to the invention are compounds wherein two adjacent groups taken from $R^2$ to $R^5$ are joined and designate —CH═CH—NH—, thereby forming a fused 5 membered ring.

In one embodiment of the invention $R^6$ to $R^9$ are independently selected from hydrogen, halogen, cyano, nitro, $C_{1-6}$-alkyl, $C_{1-6}$-alkoxy, $C_{1-6}$-alkylthio, hydroxy, $C_{3-8}$-cycloalkyl, $C_{3-8}$-cycloalkyl-$C_{1-6}$ alkyl, trifluoromethyl, and $C_{1-6}$ alkylsulfonyl, or two adjacent groups taken from $R^6$–$R^9$ may be joined and designate a methylenedioxy group, in particular $R^6$ to $R^9$ are independently selected from hydrogen, halogen, $C_{1-6}$-alkyl, $C_{1-6}$-alkoxy, or two adjacent groups taken from $R^6$–$R^9$ may be joined and designate a methylenedioxy group.

A subgroup of compounds are the compounds wherein at least one of $R^8$ and $R^9$ is hydrogen and $R^6$ to $R^7$ are independently hydrogen or halogen, in particular chloro.

Specific examples of $R^{11}$ and $R^{12}$ are hydrogen or $C_{1-6}$-alkyl, and $RI^0$ is hydrogen, $C_{1-6}$-alkyl, or acyl.

Preferred compounds are compounds selected from
6-Chloro-3-[[1-(6-bromo-1-indanylmethyl)- 1 ,2,3,6-tetrahydropyridin-4-yl]-1H-indole,
3-[1-(1-Indanylmethyl)-1,2,3,6-tetrahydropyridin4-yl]-1H-indole,
3-[1-(1-Indanylmethyl)piperindin4-yl]-1H-indole,
6-Chloro-3-[1-(7-methoxyindan-1-yl)methyl-1,2,3,6-tetrahydropyridin-4-yl]-1H-indole.

3-[1-(6-Methoxyindan-1-yl)methyl-1,2,3,6-tetrahydropyridin-4-yl]-1H-indole, oxalate,
6-Chloro-3-[1-(6-cyano-1-indanylmethyl)-1,2,3,6-tetrahydropyridin-4-yl]-1H-indole,
6-Chloro-3-[1-(6-cyano-1-indanylmethyl)piperidin-4-yl]-1H-indole,
6-Chloro-3-[1-(4-acetylamino-1-indanylmethyl)-1,2,3,6-tetrahydropyridin-4-yl]-1H-indole,
6-Chloro-3-[-(5-acetylamino-1-indanylmethyl)-1,2,3,6-tetrahydropyridin-4-yl]-1H-indole,
6-Chloro-3-[1-(6-bromo-1-indanylmethyl)-1,2,3,6-tetrahydropyridin-4-yl]-1H-indole,
6-Chloro-3-[1-[2-(indane-1-yl)ethyl]-1,2,3,6-tetrahydropyridine-4-yl]-1H-indole,
5-Fluoro-3-[1-[2-(indan-1-yl)ethyl]-1,2,3,6-tetrahydropyridin-4-yl]-1H-indole,
5-Fluoro-3-[1-[2-(indan-1-yl)ethyl]-piperidin4-yl]-1H-indole,
5-Fluoro-3-[1-[4-(indan-1-yl)butan-1-yl]-1,2,3,6-tetrahydropyridin-4-yl]-1H-indole,
5-Fluoro-3-[1-[4-(indan-1-yl)butan-1-yl]-piperidin-4-yl]-1H-indole,
6-Chloro-3-[1-[4-(indan-1-yl)butan-1-yl]-piperidin-4-yl]-1H-indole,
6-Chloro-3-[1-[3-(indan-1-yl)propan-1-yl]-1,2,3,6-tetrahydropyridin-4-yl]-1H-indole,
6-Chloro-3-[1-[4-(indane-1-yl)butan-1-yl]-1,2,3,6-tetrahydropyridin-4-yl]-1H-indole,
6-Chloro-3-[1-(indan-2-yl)methyl-1,2,3,6-tetrahydropyridin-4-yl]-1H-indole,
3-[1-(Indan-2-yl)methyl-1,2,3,6-tetrahydropyridin-4-yl]-1H-indole,
7-Chloro-3-[1-(indan-2-yl)methyl-1,2,3,6-tetrahydropyridin-4-yl]-1H-indole,
6,7-Dichloro-3-[1-(indan-2-yl)methyl-1,2,3,6-tetrahydropyridin-4-yl]-1H-indole,
3-[1-(Indan-2-yl)methyl-1,2,3,6-tetrahydropyridin-4-yl]-5,6-methylenedioxy-1H-indole,
5-[4-(Indan-2-yl)methylpiperazin-1-yl]-1H-indole,
6-Chloro-3-[1-[2-(indan-2-yl)ethyl]-1,2,3,6-tetrahydropyridin-4-yl]-1H-indole,
6-Chloro-3-[1-[3-(indan-2-yl)propan-1-yl]-1,2,3,6-tetrahydropyridin-4-yl]-1H-indole,
6-Chloro-3-[1-[4-(indan-2-yl)butan-1-yl]-1,2,3,6-tetrahydropyridin4-yl]-1H-indole,
3-[1-[(4-(2-Propyl)oxyindan-2-yl)methyl]piperidin-4-yl]-6-chloro-1H-indole,
4-[4-(6-Chloro-1H-indol-3-yl)-1,2,3,6-tetrahydropyridin-1-ylmethyl]-1,4,5,6-tetrahydrocyclopent[e]indole,
6-Chloro-3-[1-(4-acetylaminoindan-2-yl)methyl-1,2,3,6-tetrahydropyridine-4-yl-1H-indole,
6-Chloro-3-[1-(4-acetylaminoindan-2-yl)methylpiperidin-4-yl]-1H-indole,
6-Chloro-3-[1-[2-(6-acetylaminoindan-1-yl)ethyl]-1,2,3,6-tetrahydropyridin-4-yl]-1H-indole,
6-Chloro-3-[1-[3-(6-acetylaminoindan-1-yl)propan-1-yl]-1,2,3,6-tetrahydropyridin-4-yl]-1H-indole,
6-Chloro-3-[1-[4-(6-acetylaminoindan-1-yl)butan-1-yl]-1,2,3,6-tetrahydropyridin-4-yl]-1H-indole,
3-[1-(5-Acetylaminoindan-2-yl)methyl-1,2,3,6-tetrahydropyridin-4-yl]-6-chloro-1H-indole,
3-[1-(5-Acetylaminoindan-2-yl)methylpiperidin-4-yl]-6-chloro-1H-indole,
3-[1-[2-(1-Acetyl-2,3-dihydro-1H-indol-3-yl)ethyl]-1,2,3,6-tetrahydropyridin-4-yl]-6-chloro-1H-indole,
3-[1-[2-(1-Acetyl-2,3-dihydro-1H-indol-3-yl)ethyl]piperidin-4-yl]-6-chloro-1H-indole, 6-Chloro-3-[1-[2-(1-formyl-2,3-dihydro-1H-indol-3-yl)ethyl]-1,2,3,6-tetrahydropyridin-4-yl]-1H-indole,
6-Chloro-3-[1-[2-(1-formyl-2,3-dihydro-1H-indol-3-yl)ethyl]piperidin-4-yl]-1H-dione,
3-[1-[2-(1-Acetyl-5-bromo-2,3-dihydro-1H-indol-3-yl)ethyl]-1,2,3,6-tetrahydropyridin-4-yl]-6-chloro-1H-indole,
3-[1-[2-(1-Acetyl-2,3-dihydro-1H-indol-3-yl)ethyl]-1,2,3,6-tetrahydropyridin-4-yl]-7-1H-indole,
3-[1-[2-(1-Acetyl-2,3-dihydro-1H-indol-3-yl)ethyl]-1,2,3,6-tetrahydropyridin-4-yl]-6,7-dichloro-1H-indole,
3-[1-[2-(1-Acetyl-2,3-dihydro-1H-indol-3-yl)ethyl]-1,2,3,6-tetrahydropyridin-4-yl]-5,6-methylenedioxy-1H-indole,
3-[1-[2-(1-tert-Butoxycarbonyl-2,3-dihydro-1H-indol-3-yl)ethyl]-1,2,3,6-tetrahydropyridin-4-yl]-6-chloro-1H-indole,
5-[4-[2-(1-Acetyl-2,3-dihydro-1H-indol-3-yl)ethyl]piperazin-1-yl]-1H-indole,
3-[1-[3-(1-Acetyl-2,3-dihydro-1H-indol-3-yl)propan-1-yl]-1,2,3,6-tetrahydropyridin-4-yl]-1H-indole,
3-[1-[2-(1-Acetyl-5-fluoro-2,3-dihydro-1H-indol-3-yl)ethyl]-1,2,3,6-tetrahydropyridin-4-yl]-6-chloro-1H-indole,
3-[1-[2-(1-Acetyl-5-methyl-2,3-dihydro-1H-indol-3-yl)ethyl]-1,2,3,6-tetrahydropyridin-4-yl]-6-chloro-1H-indole,
6-Chloro-3-[1-(indan-2-ylmethyl)piperidin-4-yl]-1H-indole,
3-[1-(Indan-2-ylmethyl)piperidin-4-yl]-1H-indole,
7-Chloro-3-[1-(indan-2-ylmethyl)piperidin-4-yl]-1H-indole,
6,7-Dichloro-3-[1-(indan-2-ylmethyl)piperidin-4-yl]-1H-indole,
3-[1-(Indan-2-ylmethyl)piperidin-4-yl]-5,6-methylenedioxy-1H-indole,
6-Chloro-3-[1-[2-(indan-2-yl)ethyl]piperidin-4-yl]-1H-indole,
6-Chloro-3-[1-[3-(indan-2-yl)propan-3-yl]piperidin-4-yl]-1H-indole,
6-Chloro-3-[1-[4-(indan-2-yl)butan-4-yl]piperidin-4-yl]-1H-indole,
4-[4-[2-(Indan-2-yl)ethyl]piperazin-1-yl]-1H-indole,
5-[4-[2-(Indan-2-yl)ethyl]piperazin-1-yl]-1H-indole,
5-Chloro-1-[1-[2-(indan-2-yl)ethyl]-1,2,3,6-tetrahydropyridin-4-yl]-1H-indole,
1-[1-[2-(Indan-2-yl)ethyl]-1,2,3,6-tetrahydropyridin-4-yl]-1H-indole,
2-[1-[2-(Indan-2-yl)ethyl]-1,2,3,6-tetrahydropyridin-4-yl]-1H-indole,
5-Chloro-1-[1-[2-(indan-2-yl)ethyl]piperidin-4yl]-1H-indole,
1-[1-[2-(Indan-2-yl)ethyl]piperidin-4-yl]-1H-indole,
6-Chloro-3-[1-[2-(2,3-dihydro-1H-indol-3-yl)ethyl]-1,2,3,6-tetrahydropyridin-4-yl]-1H-indole,
6-Chloro-3-[1-[4-(2,3-dihydro-1H-indol-3-yl)butyl]-1,2,3,6-tetrahydropyridin-4-yl]-1H-indole,
6-Chloro-3-[1-[2-(2,3-dihydro-1-methylaminocarbonyl-1H-indol-3-yl)ethyl]-1,2,3,6-tetrahydropyridin-4-yl]-1H-indole,
(+)-(3-[1-[2-(1-Acetyl-2,3-dihydro-1H-indol-3-yl)ethyl]-1,2,3,6-tetrahydropyridin-4-yl]-6-chloro1H-indole,
(−)-(3-[1-[2-(1-Acetyl-2,3-dihydro-1H-indol-3-yl)ethyl]-1,2,3,6-tetrahydropyridin-4-yl]-6-1H-indole,
3-[1-[4-(1-Acetyl-2,3-dihydro-1H-indol-3-yl)butyl]-1,2,3,6-tetrahydropyridin-4-yl]-6-chloro-1H-indole,
6-Chloro-3-[1-[6-chloro-1-indanylmethyl]-1,2,3,6-tetrahydropyridin-4-yl]-1H-indole,
6-Chloro-3-[1-[6-nitro-1-indanylmethyl]-1,2,3,6-tetrahydropyridin-4-yl]-1H-indole,
6-Chloro-3-[1-[6-fluoro-1-indanylmethyl]1,2,3,6-tetrahydropyridin-4-yl]-1H-indole,
6-Chloro-3-[1-[5-chloro-1-indanylmethyl]-1,2,3,6-tetrahydropyridin-4-yl]-1H-indole,
6-Chloro-3-[1-[6-methyl-1-indanylmethyl]-1,2,3,6-tetrahydropyridin-4-yl]-1H-indole,
6-Chloro-3-[1-(1-indanylmethyl)-1,2,3,6-tetrahydropyridin-4-yl]-1-methyl-1H-indole,
6-Chloro-3-[1-(1-indanylmethyl)-1,2,3,6-tetrahydropyridin-4-yl]-1-(2-propyl-1H-indole,
5-Fluoro-3-[1-[6-(trifluoromethyl)-1-indanylmethyl]-1,2,3,6-tetrahydropyridin-4-yl]-1H-indole,
5-Fluoro-3-[1-[5-(trifluoromethylsulfonyloxy)-1-indanylmethyl]-1,2,3,6-tetrahydropyridin-4-yl]-1H-indole,
6-Chloro-3-[1-[1-indanylmethyloxyethyl]-1,2,3,6-tetrahydropyridin-4-yl]-1H-indole,
5-Fluoro-3-[1-[6-(indan-1-yl)hexan-1-yl]-1,2,3,6-tetrahydropyridin-4-yl]-6-chloro-1H-indole,
3-[1-[2-(1-Acetyl-5-fluoro-2,3-dihydro-1H-indol-3-yl)ethyl]piperidin-4-yl]-6-chloro-1H-indole,
6-Chloro-3-[1-[2-(1-formyl-5-fluoro-2,3-dihydro-1H-indol-3-yl)ethyl]-1,2,3,6-tetrahydropyridin-4-yl]-1H-indole,
6-Chloro-3-[1-[2-(5-fluoro-2,3-dihydro-1H-indol-3-yl)ethyl]-1,2,3,6-tetrahydropyridin-4-yl]-1H-indole,
6-Chloro-3-[1-[2-(5-fluoro-2,3-dihydro-1-methylaminocarbonyl-1H-indol-3-yl)ethyl]-1,2,3,6-tetrahydropyridin-4-yl]-1H-indole,
6-Chloro-3-[1-[2-(2,3-dihydro-1-mesylaminocarbonyl-1H-indol-3-yl)ethyl]-1,2,3,6-tetrahydropyridin-4-yl]-1H-indole,
6-Chloro-3-[1-[2-(5-fluoro-2,3-dihydro-1-mesylaminocarbonyl-1H-indol-3-yl)ethyl]-1,2,3,6-tetrahydropyridin-4-yl]-1H-indole,
3-[1-[(1-Acetyl-2.3-dihydro-1H-indol-2-yl)methyl]-1,2,3,6-tetrahydropyridin-4-yl]-6-chloro-1H-indole,
3-[1-[(1-Acetyl-5-fluoro-2,3-dihydro-1H-indol-2-yl)methyl]-1,2,3,6-tetrahydropyridin-4-yl]-6-chloro-1H-indole,
3-[1-[(1-Acetyl-2,3-dihydro-1H-indol-2-yl)methyl]piperidin-4-yl]-6-chloro-1H-indole,
3-1-[2-(1-Acetyl-2,3-dihydro-1H-indol-2-yl)ethyl]-1,2,3,6-tetrahydropyridin-4-yl]-6-chloro-1H-indole,
3-[1-[2-(1-Acetyl-5-fluoro-2,3-dihydro-1H-indol-2-yl)ethyl]-1,2,3,6-tetrahydropyridin-4-yl]-6-chloro-1H-indole,
3-[1-[2-(1-Acetyl-2,3-dihydro-1H-indol-2-yl)ethyl]piperidin-4-yl]-6-chloro-1H-indole,
6-Chloro-3-[1-[2-(2,3-dihydro-1H-indol-2-yl)ethyl]-1,2,3,6-tetrahydropyridin-4-yl]-1H-indole,
6-Chloro-3-[1-[2-(5-fluoro-2,3-dihydro-1H-indol-2-yl)ethyl]-1,2,3,6-tetrahydropyridin-4-yl]-1H-indole,
6-Chloro-2-[4-[(indan-2-yl)methyl]piperazin-1-yl]-1H-indole,
6-Chloro-2-[4-[2-(indan-2-yl)ethyl]piperazin-1-yl]-1H-indole,
2-[4-[2-(1-Acetyl-2,3-dihydro-1H-indol-3-yl)ethyl]piperazin-1-yl]-6-chloro-1H-indole,
2-[4-[2-(1-Acetyl-5-fluoro-2,3-dihydro-1H-indol-3-yl)ethyl]piperazin-1-yl]-6-chloro-1H-indole,
6-Chloro-3-[4-[(indan-2-yl)methyl]piperazin-1-yl]-1H-indole,
6-Chloro-3-[4-[2-(indan-2-yl)ethyl]piperazin-1-yl]-1H-indole,
3-[4-[2-(1-Acetyl-2,3-dihydro-1H-indol-3-yl)ethyl]piperazin-1-yl]-6-chloro-1H-indole, 3-[4-[2-(1-Acetyl-5-fluoro-2,3-dihydro-1H-indol-3-yl)
  ethyl]piperazin-1-yl]-6-chloro-1H-indole,
4-[4-[(Indan-2-yl)methyl]piperazin-1-y]-1H-indole,
4-[4-[2-(1-Acetyl-2,3-dihydro)-1H-indol-3-yl)ethyl]
  piperazin-1-yl]-1H-indole,
4-[4-[2-(1-Acetyl-5-fluoro-2,3-dihydro-1H-indol-3-yl)
  ethyl]piperazin-1-yl]-1H-indole,
7-[4-[(Indan-2-yl)methyl]piperazin-1-yl]-1H-indole,
7-[4-[2-(Indan-2-yl)ethyl]piperazin-1-yl]-1H-indole,
7-[4-[2-(1-Acetyl-2,3-dihydro-1H-indol-3-yl)ethyl]
  piperazin-1-yl]-1H-indole,
7-[4-[2-(1-Acetyl-5-fluoro-2,3-dihydro-1H-indol-3-yl)
  ethyl]piperazin-1-yl]-1H-indole,
2-[1-[2-(1-Acetyl-2,3-dihydro-1H-indol-3-yl)ethyl]-1,2,3,6-
  tetrahydropyridin-4-yl]-1H-indole,
2-[1-[2-(1-Acetyl-2,3-dihydro-1H-indol-3-yl)ethyl]-1,2,3,6-
  tetrahydropyridin-4-yl]-5-chloro-1H-indole,
2-[1-[2-(1-Acetyl-2,3-dihydro-1H-indol-3-yl)ethyl]
  piperidin-4-yl]-1H-indole,
2-[1-[2-(1-Acetyl-2,3-dihydro-1H-indol-3-yl)ethyl]
  piperidin-4-yl]-5-chloro-1H-indole,
2-[1-(Indan-2-yl)methyl-1,2,3,6-tetrahydropyridin-4-yl]-
  1H-indole,
5-Chloro-2-[1-(indan-2-yl)methyl-1,2,3,6-
  tetrahydropyridin-4-yl]-1H-indole,
5-Chloro-2-[1-[2-(indan-2-yl)ethyl]-1,2,3,6-
  tetrahydropyridin-4-yl]-1H-indole,
2-[1-(Indan-2-yl)methylpiperidin-4-yl]-1H-indole,
5-Chloro-2-[1-(indan-2-yl)methylpiperidin-4-yl]-1H-
  indole,
2-[1-[2-(Indan-2-yl)ethyl]piperidin-4-yl]-1H-indole,
5-Chloro-2-[1-[2-(indan-2-yl)ethyl]piperidin-4-yl]-1H-
  indole,
7-[4-[(6-Chloro-1H-indol-3-yl)-1,2,3,6-tetrahydropyridin-
  1-yl]methyl]-3,6,7,8-tetrahydrocyclopent[e]indole,
7-[4-[(6-Chloro-1H-indol-3-yl)-1,2,3,6-tetrahydropyridin-
  1-yl]methyl]-1,5,6,7-tetrahydrocyclopent[f]indole,
6-[4-[(6-Chloro-1H-indol-3-yl)-1,2,3,6-tetrahydropyridin-
  1-yl]methyl]-1,6,7,8-tetrahydrocyclopent[g]indole,
7-[4-[(6-Chloro-1H-indol-3-yl)-1,2,3,6-tetrahydropyridin-
  1-yl]methyl]-1,6,7,8-tetrahydrocyclopent[g]indole,
(+)6-Chloro-3-[1-[2-(2,3-dihydro-1H-indol-3-yl)ethyl]-1,2,
  3,6-tetrahydropyridin-4-yl]-1H-indole,
6-Chloro-3-[1-[2-(2,3-dihydro-1H-indol-1-yl)ethyl]-1,2,3,
  6-tetrahydropyridin-4-yl]-1H-indole
6-Chloro-3-[1-[2-(2,3-dihydro-1H-indol-1-yl)ethyl]
  piperidin-4-yl]-1H-indole,
6-Chloro-3-[1-[3-(2,3-dihydro-1H-indol-1-yl)propan-1-yl]-
  1,2,3,6-tetrahydropyridin-4-yl]-1H-indole,
6-Chloro-3-[1-[4-(2,3-dihydro-1H-indol-1-yl)butan-1-yl]-1,
  2,3,6-tetrahydropyridin-4-yl]-1H-indole,
6-Chloro-3-[1-[3-(2,3-dihydro-1H-indol-1-yl)-3-
  oxopropan-1-yl]-1,2,3,6-tetrahydropyridin-4-yl]-1H-
  indole,
3-[1-[(5-(2-Propyl)oxyindan-2-yl)methyl]piperidin-4-yl]-6-
  chloro-1H-indole,
3-[1-[(5,6-Dimethoxyindan-2-yl)methyl]piperidin-4-yl]-6-
  chloro-1H-indole,
3-[1-[(4-(2-Propyl)oxyindan-1-yl)methyl]piperidin-4-yl]-6-
  chloro-1H-indole,
3-[1-[(5-(2-Propyl)oxyindan-1-yl)methyl]piperidin-4-yl]-6-
  chloro-1H-indole,
3-[1-[(7-Methoxyindan-1-yl)methyl]piperidin-4-yl]-6-
  chloro-1H-indole,
3-[1-[(5,6-Dimethoxyindan-1-yl)methyl]piperidin-4-yl]-6-
  chloro-1H-indole,
3-[1-[(4-(2-Propyl)oxyindan-2-yl)methyl]-1,2,3,6-
  tetrahydropyridin-4-yl]-6-chloro-1H-indole,
3-[1-[(5-(2-Propyl)oxyindan-2-yl)methyl]-1,2,3,6-
  tetrahydropyridin-4-yl]-6-chloro-1H-indole,
3-[1-[(5,6-Dimethoxyindan-2-yl)methyl]-1,2,3,6-
  tetrahydropyridin-4-yl]-6-chloro-1H-indole,
3-[1-[(4-(2-Propyl)oxyindan-1-yl)methyl]-1,2,3,6-
  tetrahydropyridin-4-yl]-6-chloro-1H-indole,
3-[1-[(5-(2-Propyl)oxyindan-1-yl)methyl]-1,2,3,6-
  tetrahydropyridin-4-yl]-6-chloro-1H-indole,
3-[1-[(7-Methoxyindan-1-yl)methyl]-1,2,3,6-
  tetrahydropyridin-4-yl]-6-chloro-1H-indole,
3-[1-[(5,6-Dimethoxyindan-1-yl)methyl]-1,2,3,6-
  tetrahydropyridin-4-yl]-6-chloro-1H-indole, or
3-[4-[(5,6-Dimethoxyindan-1-yl)methyl]-piperazin-1-yl]-6-
  chloro-1H-indole,
and pharmaceutically acceptable acid addition salts thereof.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The compounds of the invention may be prepared as follows:

1) Alkylating a piperazine, piperidine, or tetrahydropyridine of the formula II with an alkylating derivative of the formula III:

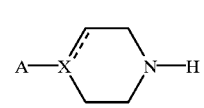

II

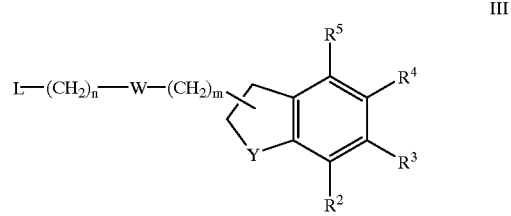

III wherein $R^2$–$R^5$, X, Y, A, n, m, W, and the dotted line are as previously defined, and L is a leaving group such as eg. halogen, mesylate, or tosylate:

2) Reducing the amide carbonyl in a compound of the following Formula IV:

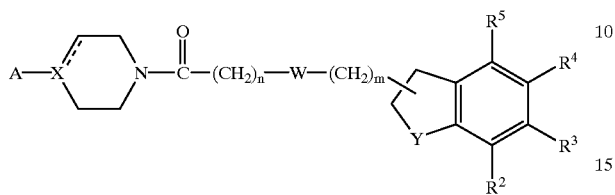

IV wherein $R^2$–$R^5$, X, Y, A, m, W and the dotted line are as previously defined and r is n–1 and n is as defined above;

3) Introducing a substituent $R^{2'}$, $R^{3'}$, $R^{4'}$ or $R^{5'}$ by reacting a compound of the following Formula V:

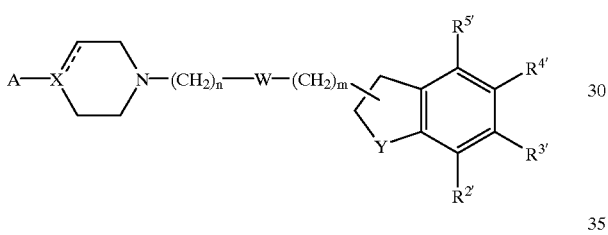

V wherein one of $R^{2'}$–$R^{5'}$ is hydrogen and the others are the corresponding $R^2$, $R^3$, $R^4$, or $R^5$ as previously defined and X, Y, A, m, n, W, and the dotted line are as previously defined, by using a reactive reagent such as a halogen or a halogenating agent, a sulfonating agent, a nitration agent or a reactive agent generating carbonium ions ($RCO^+$, $R^+$) wherein R is alkyl alkynyl, aryl cycloalkyl, or cycloalk(en/yn)yl;

4) Reducing the double bond in an indole compound of the following Formula VI:

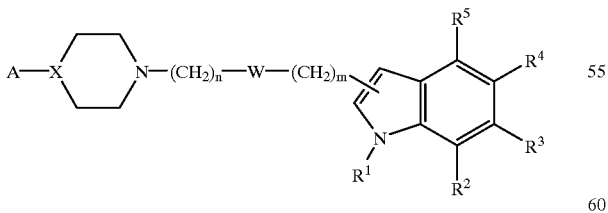

VI wherein $R^2$–$R^5$, $R^1$, X, n, m, W, and A are as previously defined;

5) Reducing the tetrahydropyridinyl double bond in derivatives of the following Formula VII

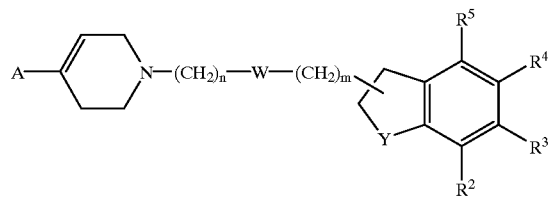

VII wherein $R^2$–$R^5$, Y, n, m, W, and A are as previously defined;

6) Reacting a dihydroindole derivative of formula VIII:

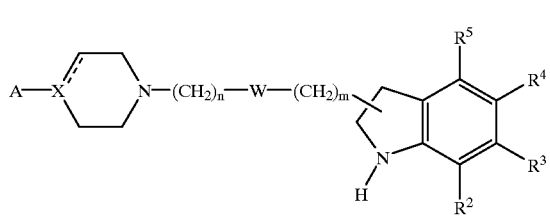

VIII wherein $R^2$–$R^5$, X, A, n, m, W, and the dotted line are as previously defined, with a reagent of the formula $R^1$—L, where L is a leaving group such as halogen, mesylate or tosylate and $R^1$ is as previously defined, or of the formula $R^{1'}$-hal or $R^{1'}$—OCOR, in which formulas hal is halogen, $R^{1'}$ is acyl, thioacyl, a group $R^{15}VCO$—, or a group $R^{16}R^{17}NCO$— or $R^{16}R^{17}NCS$— where $R^{15}$, V, $R^{16}$ and $R^{17}$ are as previously defined except that neither $R^{16}$ nor $R^{17}$ may be hydrogen, or with a lower alkylsulfonyl halogenide, trifluoromethylsulfonyl halogenide or an isocyanate or thioisocyanate of the formula $R^{16}$—N=C=O or $R^{16}$—N=C=S wherein $R^{16}$ is as previously defined;

7) Reacting an anilino derivative of the formula IX:

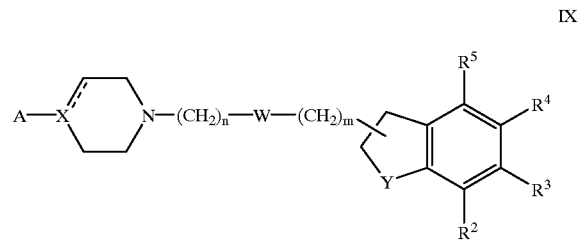

IX wherein one of $R^2$–$R^5$ is $NHR^{14}$, and $R^{14}$ is defined as above and the other $R^2$–$R^5$, X, Y, A, n, m, W, and the dotted line are as previously defined, with a reagent of the formula $R^{13}$—L, where L is a leaving group such as halogen, mesylate or tosylate and $R^{13}$ is as previously defined, or of the formula $R^{13'}$-hal or $R^{13'}$—OCOR, in which formulas hal is halogen, $R^{13'}$, is acyl, thioacyl, a group $R^{15}VCO$—, or a group $R^{16}R^{17}NCO$— or $R^{16}R^{17}NCS$— where $R^{15}$, V, $R^{16}$ and $R^{17}$ are as previously defined except that neither $R^{16}$ nor $R^{17}$ may be hydrogen, or with a lower alkylsulfonyl halogenide, trifluoromethylsulfonyl halogenide or an isocyanate or thioisocyanate of the formula $R^{16}$—N=C=O or $R^{16}$—N=C=S wherein $R^{16}$, is as previously defined;

8) Alkylating a dihydroindole derivative of the Formula X with an alkylating derivative of the Formula XI:

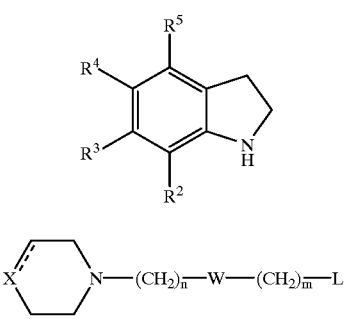

wherein $R^2$–$R^5$, X, A, n, m, W, and the dotted line are as previously defined, and L is a leaving group such as eg. halogen, mesylate, or tosylate; or 9) reducing the carbonyl amide compounds of Formula XII:

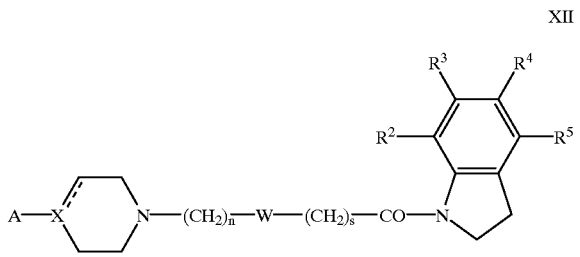

wherein $R^2$–$R^5$, X, A, n, W and the dotted line are as previously defined and s is m−1 and m is as defined above; whereupon the compound of Formula I is isolated as the free base or a pharmaceutically acceptable acid addition salt thereof.

The reaction in Methods 6) and 7) are conveniently performed at low temperature (eg. below room temperature) in an inert solvent such as acetone, dichloromethane, tetrahydrofuran or dimethoxyethane when reactive carboxylic acid chlorides, isocyanates, or isothiocyanates are used. Formulated amines are prepared from the corresponding amines by reaction in formic acid, with esters of formic acid, or by reaction with mixed formic acid anhydride prepared in situ. Generally, reaction temperatures are between 0° C. and the boiling point of the formyl precursor compounds.

The alkylations according to Methods 1) and 8) are generally performed by refluxing in a suitable solvent such as acetone, methyl isobutyl ketone, tetrahydrofuran, dioxane, ethanol or 2-propanol in the presence of a base such as triethylamine or potassium carbonate.

The reductions of double bonds according to Methods 4) and 5) are generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran, dioxane, or diethyl ether.

The reductions according to Methods 2) and 9) are generally performed by use of $LiAlH_4$, $AlH_3$ or diborane in an inert solvent such as tetrahydrofuran, dioxane, or diethyl ether at room temperature or at a slightly elevated temperature.

The halogenation according to Method 3) is generally performed by use of chlorine, bromine, or N-chlorosuccinimide, N-bromosuccinimide or another halogen precursor molecule, conveniently in the presence of a catalyst such as Fe ions or a mineral acid.

The indoles 7-chloro-1H-indole and 6,7-dichloro-1H-indole were prepared in accordance with the procedure of G. Bartoli et al., Tetrahedron Lett. 1989, 30, 2129–2132. The two piperazinylindoles 4-(piperazin-1-yl)-1H-indole and 5-(piperazin-1-yl)-1H-indole have been described in the literature, WO patent publication No. 95/33743 and U.S. Pat. No. 5,576,319.

Synthesis of 3-(piperidin-4-yl)-1H-indoles and 3-(1,2,3,6-tetrahydropyridin-4-yl)-1H-indoles have been described in the literature EP-A1-465398.

Key intermediates such as 1-indanecarboxylic acid ( V. Asham and W. H. Linnell, J. Chem. Soc. 1954, 4691–4693, Hansen et al. Helv.Chim.Acta 1982, 33, 325–343) and 6-nitro-1-indanecarboxylic acid (G.Kirsch et al. Just. Lieb. Ann. Chem. 1976, 10, 1914) were prepared according to well-known literature procedures. (Indan-2-yl)acetic acid, 3-(indan-2-yl)propionic acid, 4-(indan-2-yl)butyric acid, and 2-(indan-2-yl)ethanol have been described in the literature (Y. Tanaka et al. J. Med. Chem. 1994, 37, 2071–2078).

Experimental Section

Melting points were determined on a Büchi SMP-20 apparatus and are not corrected. Mass spectra were obtained on a Quattro MS-MS system from VG Biotech, Fisons Instruments. The MS-MS system was connected to an HP 1050 modular HPLC system. A volume of 20–50 $\mu$l of the sample (10 $\mu$g/ml) dissolved in a mixture of 1% acetic acid in acetonitril/water 1:1 was introduced via the autosampler at a flow of 30 $\mu$l/min into the Electrospray Source. Spectra were obtained at two standard sets of operating conditions. One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+) this ion was only present under the first set of operating conditions. 1H NMR spectra were recorded of all novel compounds at 250 MHz on a Bruker AC 250 or at 500 MHz on Bruker Avance DRX 500 instrument. Deuterated chloroform (99.8% D) or dimethylsulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230–400 mesh ASTM was used.

EXAMPLE 1

1-Indanylmethanol, 1a (Intermediate)

To a suspension of $LiAlH_4$ (4.7 g) in diethyl ether (200 ml) was added dropwise a solution of $AlCl_3$ in diethyl ether (200 ml). A solution of 1-indanecarboxylic acid (10 g) (prepared according to the method of Hansen et al. *Helv. Chim. Acta* 1982, 33, 325–343) in dry tetrahydrofuran (200 ml) was added drop-wise at 10–15° C. The mixture was finally stirred at room temperature for 1.5 hours. Excess AlH$_3$ was destroyed by addition of concentrated aqueous NaOH solution (25 ml) at 0° C. Precipitated inorganic salts were filtered off and the solvents evaporated in vacuo leaving 6.8 g of the title compound 1a as a viscous oil which was used without further purification.

The following 1-indanylmethanols were prepared in a similar manner:

6-Bromo-1-indanylmethanol from alane reduction of the corresponding methyl 6-bromo-1-indanecarboxylic acid ester, isolated as a viscous oil. 1b.

EXAMPLE 2

6-Cyano-1-indanylmethanol 2a (Intermediate)

To a solution of 6-bromo-1-indanylmethanol (20 g) in N-methyl-2-pyrrolidone (NMP) (380 ml) was added CuCN (79 g). The mixture was heated at 160° C. for 6 hours. After cooling to 80–90° C. the mixture was poured into an aqueous solution (500 ml) of NaCN (4g). After stirring for 20 minutes excess CuCN was filtered off. Ethyl acetate (300 ml) was added and the organic phase was separated and worked-up. The remaining oil was dissolved in diethyl ether (300 ml) and washed with saturated brine (2×100 ml). The organic phase was separated and worked-up according to the general procedure leaving 14.6 g of crude title compound 2a as a viscous oil. Column chromatography on silica gel (eluent:ethylacetat/heptane 6:4) afforded pure 2a (8.7 g) which was used without further purification.

EXAMPLE 3

6-Cyano-1-indanylmethanol methanesulfonate, 3a (Intermediate)

To a solution of 6-cyano-1-indanylmethanol 2a (3 g) and triethylamine (2.8 ml) in dichloromethane (50 ml) was added drop-wise a solution of methansulfonylchloride (1.5 ml) in dichloromethane (25 ml) at 0° C. The mixture was stirred at room temperature for 1 hour. Water was added (200 ml) and the organic phase was subsequently separated and worked-up according to the standard procedure above. The remaining crystalline product was stirred with diethyl ether and filtered off. Yield 2.7 g Mp 62–63° C.

The following methanesulfonates were prepared in a similar manner:

1-Indanylmethanol methanesulfonate, 3b. Isolated as a viscous oil
6-Bromo-1-indanylmethanol methanesulfonate, 3c.
6-Nitro-1-indanylmethanol methanesulfonate, 3d
6-Chloro-1-indanylmethanol methanesulfonate, 3e

EXAMPLE 4

3-1-(1-indanylcarbonyl)-1,2,3,6-tetrahydropyridin-4-yl)-1H-indole, 4a

1-Indanecarboxylic acid chloride (4.5 g), prepared as described in International Patent Application No. WO 9533721-A1 in dichloromethane (25 ml) was added drop-wise at 0–5° C. to a mixture of 3-(1,2,3,6-tetrahydropyridin-4-yl)-1H-indole (5 g) (see general method for preparation in Guillaume et al. *Eur. J. Med. Chem.* 1987, 22, 33–43) and triethylamine (3.8 ml) in THF (50 ml). The resulting mixture was stirred overnight at room temperature. The mixture was poured into diluted aqueous NH$_4$OH (500 ml) and extracted several times with dichloromethane (4×100 ml). The combined organic phases were worked up according to the general procedure above. Column chromatography (eluted with ethyl acetate/heptane 70/30) of the crude product afforded pure title compound 4a as a viscous oil (4.7 g) which was used without further purification.

In a similar manner was prepared the following amides were prepared:

3-[1-(1-Indanylcarbonyl)piperidin-4-yl]-1H-indole 4b isolated as an oil.
6-Chloro-3-[1-(7-methoxy-1-indanylcarbonyl)-1,2,3,6-tetrahydropyridin-4-yl]-1H-indole, 4c. From compound 23a and 6-chloro-3-(1,2,3,6-tetrahydropyridin-4-yl)-1H-indole.
3-[1-(6-Methoxy-1-indanylcarbonyl)-1,2,3,6-tetrahydropyridin-4-yl]-1H-indole 4d. From compound 23b and 3-(1,2,3,6-tetrahydropyridin-4-yl)-1H-indole.

EXAMPLE 5

3-[1-(1-Indanylmethyl)-1,2,3,6-tetrahydropyridin-4-yl]-1H-indole, 5a

To a solution of LiAlH$_4$ (1.6 g) in dry THF (100 ml) kept at 0° C. was added drop-wise a solution of 3-[1-(1-indanylcarbonyl)-1,2,3,6-tetrahydropyridin-4-yl]-1H-indole 4a (4.7 g) in dry THF (200 ml). The mixture was left stirring over-night at room temperature. Excess LiAlH$_4$ was destroyed by cautiously adding 10% water in THF. The precipitated inorganic salts were filtered off. The solvents were evaporated leaving crude title compound (5.2 g). Recrystallization from 2-propanol afforded 2.8 g of pure 5a. Mp 168–170° C. $^1$H NMR (CDCl$_3$): δ1.85–2.00 (m, 1H); 2.30–2.45 (m, 1H); 2.60 (dd, 1H); 2.60–2.70 (m, 2H); 2.70–3.00 (m, 5H); 3.30 (broad t, 2H); 3.45 (quin, 1H); 6.25 (broad t, 1H); 7.10–7.25 (m, 6H); 7.30–7.40 (m, 2H); 7.90 (d, 1H); 8.10 (broad s, 1H). MS m/z (%): 329 (MH+, 2%), 160 (10%), 131 (100%), 91 (19%).

In a similar manner the following indanemethylamines were prepared:

3-[1-(1-Indanylmethyl)piperindin-4-yl]-1H-indole fumarate, 5b.

Prepared from compound 4b. Mp 216–218° C. $^1$H NMR (DMSO-d$_6$): δ1.70–2.00 (m, 5H); 2.20–2.35 (m, 1H); 2.40–2.50 (m, 2H); 2.65 (dd, 1H); 2.80–3.00 (m, 4H); 3.20 (broad t, 2H); 3.45 (quin, 1H); 6.60 (s, 2H); 6.95 (t, 1H); 7.05 (t, 1H); 7.15–7.30 (m, 4H); 7.30–7.40 (m, 2H); 7.60 (d, 1H); 10.80 (s, 1H). MS m/z (%): 331 (MH+, 15%), 214 (18%), 131 (100%).

6-Chloro-3-[1-(7-methoxyindan-1-yl)methyl-1,2,3,6-tetrahydropyridin-4-yl]-1H-indole, 5c.

Prepared from compound 4c. Mp 177–178° C. $^1$H NMR (CDCl$_3$) δ2.15–2.30 (m, 2H), 2.45 (t, 1H), 2.55 (broad s, 2H), 2.65–2.70 (m, 1H), 2.75–2.90 (m, 2H), 2.90–3.00 (m, 1H), 3.00–3.10 (m, 1H), 3.25 (d, 1H), 3.40 (d, 1H), 3.60–3.65 (m, 1H), 3.85 (s, 3H), 6.20 (broad s, 1H), 6.70 (d, 1H), 6.85 (d, 1H), 7.05–7.20 (m, 3H), 7.30 (s, 1H), 7.80 (d, 1H), 8.25 (broad s, 1H). MS m/z (%): 393 (MH+) 190 (25%), 161 (100%).

3-[1-(6-methoxyindan-1-yl)methyl-1,2,3,6-tetrahydropyridin-4-yl]-1H-indole oxalate, 5d.

Prepared form compound 4d. Mp 118–120° C. $^1$H NMR (DMSO-d$_6$) δ1.90–2.00 (m, 1H), 2.35–2.45 (m, 1H), 2.70–2.95 (m 4H), 3.15 (t, 1H), 3.45 (broad s, 2H), 3.50–3.65 (m, 2H), 3.75 (s, 3H), 3.95 (broad s, 2H), 6.20 (broad s, 1H), 6.75 (d, 1H), 6.95 (s, 1H), 7.10 (t, 1H), 7.10–7.20 (m, 2H), 7.45 (d, 1H), 7.55 (s, 1H), 7.85 (d, 1H), 11.35 (broad s, 1H). MS m/z (%): 359 (MH+, 6%) 190 (15%), 161 (100%), 147 (74%).

EXAMPLE 6

6-Chloro-3-[1-(6-cyano-1-indanylmethyl)-1,2,3,6-tetrahydropyridin-4-yl]-1H-indole, 6a A mixture of 6-cyano-1-indanylmethanol methanesulfonate, 3a (1.3 g), 6-chloro-3-(1,2,3,6-tetrahydropyridin-4-yl)-1H-indole (2.5 g), and potassium carbonate (1.9 g) in NMP (50 ml) was heated at 110° C. for 5 hours. After cooling to room temperature the mixture was poured into water (500 ml) and ethyl acetate (100 ml) was added. Work up according to the general procedure above afforded 4.7 g of impure product. Column chromatography (eluted with ethyl acetate/heptane/ethanol/triethylamine 30/60/10/4) afforded 1.5 g of pure compound, the crystalline product was stirred with diethyl ether and subsequently filtered. Mp 175–177° C. $^1$H NMR (CDCl$_3$): δ1.85–2.00 (m, 1H); 2.35–2.45 (m, 1H); 2.50–3.00 (m, 8H); 3.30 (broad t, 2H); 3.45 (quin, 1H); 6.15 (broad t, 1H); 7.05 (dd, 1H); 7.20–7.85 (m, 2H); 10.60 (broad s, 1H). MS m/z (%): 388 (MH+, 4%), 185 ((40%), 156 (100%), 129 (53%).

In a similar manner were prepared the following indanemethylamines:

6-Chloro-3-[1-(6-cyano-1-indanylmethyl)piperidin-4-yl]-1H-indole,hemifumarate, 6b.

Prepared from compound 3a. Mp 175–177° C. $^1$H NMR (DMSO-d$_6$): δ1.65–2.00 (mn 5H); 2.20–2.30 (m, 3H); 2.40–2.50 (m, 2H); 2.65 (dd, 1H); 2.70–3.15 (m, 4H); 3.45 (quin, 1H); 6.60 (s, 1H); 6.95 (dd, 1H); 7.15 (d, 1H); 7.35 (d, 1H); 7.45 (d, 1H); 7.55–7.65 (m, 2H); 7.80 (s, 1H); 10.95 (s, 1H). Ms m/z (%): 392 (17%), 390 (MH+, 47%), 239 (100%), 156 (69%).

6-Chloro-3-[1-(4-acetylamino-1-indanylmethyl)-1,2,3,6-tetrahydropyridin-4-yl-1H-indole, 6c.

Mp 189–190° C. $^1$H NMR (DMSO-d$_6$): δ1.65–1.90 (m, 1H); 2.05 (s, 3H); 2.10–2.30 (m, 1H); 2.40–2.95 (m, 8H); 3.20 (broad s, 2H); 3.45 (quin, 1H); 6.15 (broad t, 1H); 7.00–7.15 (m, 3H); 7.40–7.50 (m, 3H); 7.85 (d, 1H); 9.25 (s, 1H); 11.25 (s, 1H). MS m/z (%): 420 (MH+, 16%), 217 (65%), 188 (100%), 146 (57%).

The last mentioned compound was prepared from 4-Acetylamino-1-indanemethanol methanesulfonate which again was obtained from 4-Amino-1-indanemethanol as follows:

4-Amino-1-indanemethanol

A mixture of 4-nitro-1-indanecarboxylic acid and 6-nitro-1-indanecarboxylic acid were obtained according to the procedure for nitration of 1-indanecarboxylic acid by G.Kirsch et al. *Just. Lieb. Ann. Chem.* 1976, 10, 1914. This mixture was reduced with alane according to the method in Example 1). A mixture (21.9 g) of the thus obtained 4-nitro- and 6-nitroindane-1-methanol was dissolved in glacial acetic acid (600 ml) and 5% Pd on carbon black (11 g) was added. The mixture was hydrogenated in a Parr apparatus below 2 ato for 2.5 hours. The catalyst was filtered off and the solvent evaporated in vacuo. Water (500 ml) and ethyl acetate (200 ml) kept at 0° C. were added. Ph was adjusted >10 by adding aqueous NaOH solution. The organic phase was separated and worked up according to the general procedure above. The 4- and 6-anilinoisomers were separated by column chromatography on silica gel (eluted with ethyl acetate/heptane 60/40). Yield of the 4-amino-1-indanemethanol as a viscous oil: 3.6 g.

4-Acetylamino-1-indanemethanol methanesulfonate

To a mixture of 4-amino-1-Indanemethanol (3.4 g) and triethylamine (8.1 ml) in dichloromethane (150 ml) was added drop-wise at −30° C. acetylchloride (1.4 ml) in dichloromethane (20 ml). The mixture was stirred for another hour while the temperature was allowed to raise to 0° C. A solution of methansulfonylchloride (1.7 ml) in dichloromethane (20 ml) was added slowly below 0° C. Finally the mixture was allowed to heat to room temperature. Water (200 ml) and dichloromethane (50 ml) were added. The organic phase was separated and worked up as above yielding the title metanesulfonate as an oil (6.7 g as crude product).

6-Chloro-3-[1-(5-acetylamino-1-indanylmethyl)-1,2,3,6-tetrahydropyridin-4-yl]-1H-indole hemifumarate, 6d.

Mp 241–242° C., $^1$H NMR (DMSO-d$_6$) d 1.70–1.90 (1H, m), 2.00 (3H, s), 2.11–2.30 (1H, m), 2.40–2.60 (2H, m), 2.60–2.95 (5H, m), 3.20 (2H, bs), 3.25–3.40 (2H, m), 6.10 (1H, s), 7.05 (1H, d), 7.25 (2H, s), 7.40 (1H, s), 7.45 (1H, d), 7.55 (1H, s), 7.85 (2, d), 9.80 (1H, bs), 11.25 (1H, bs). MS m/z (%): 420 (MH+, 5%), 188 (100%), 146 (100%), 217 (31%), 147 (27%).

The last mentioned compound was prepared from 5-Acetylamino-1-indanemethanol methanesulfonate which again was prepared from 6-chloro-5-nitro-1-indanecarboxylic acid (G. Kirch et al,*Lieb. Ann. Chem.*, 1976, 10, 1914), in a similar manner as the above described synthesis of 4-Acetylamino-1-indanemethanol methanesulfonate.

6-Chloro-3-[1-(6-bromo-1-indanylmethyl)-1,2,3,6-tetrahydropyridin-4-yl]-1H-indole, 6e.

Prepared from compound 3c. Mp 153–155° C. $^1$H NMR (CDCl$_3$) d 1.85–1.95 (m, 1H), 2.30–2.40 (m, 1H), 2.50–2.65 (m, 3H), 2.65–2.90 (m, 5H), 3.25 (broad s, 2H), 3.45 (p, 1H), 6.20 (broad s, 1H), 7.00–7.20 (m, 3H), 7.25 (s, 1H), 7.30 (d, 1H), 7.50 (s, 1H), 7.80 (d, 1H), 8.15 (broad s, 1H). Ms m/z (%): 443 (MH+, 7%), 441 (MH+, 7%), 240 (50%), 238 (49%), 211 (59%), 209 (62%), 130 (100%).

5-Fluoro-3-[1-(6-nitro-1-indanylmethyl)-1,2,3,6-tetrahydropyridin-4-yl]-1H-indole hemifumarate, 6f.

Prepared from compound 3d. Mp>300° C. $^1$H NMR (DMSO-d$_6$) d 1.85–1.95 (m, 1H), 2.30–2.40 (m, 1H), 2.50–2.60 (m, 3H), 2.70–3.05 (m, 5H), 3.25 (broad dd, 2H), 3.50 (p, 1H), 6.10 (broad s, 1H), 6.60 (s, 1H), 6.95 (t, 1H), 7.35 (dd, 1H), 7.45–7.50 (m, 2H), 7.55 (d, 1H), 8.05 (d, 1H), 8.25 (s, 1H), 11.25 (s, 1H). MS m/z (%): 392 (MH+, 5%), 205 (29%), 176 (46%), 130 (100%).

5-Fluoro-3-[1-(6-nitro-1-indanylmethyl)-piperidin-4-yl]-1H-indole 6g.

Mp>300° C. $^1$H NMR (CDCl$_3$) d 1.75–1.95 (m, 3H), 2.00–2.10 (m, 2H), 2.25 (t, 2H), 2.30–2.40 (m, 1H), 2.45–2.65 (m, 2H), 2.75 (tt, 1H), 2.85–3.15 (m, 4H), 3.45 (p, 1H), 6.95 (dt, 1H), 7.15 (d, 1H), 7.20–7.30 (m, 3H), 7.95 (broad s, 1H), 8.05 (dd, 1H), 8.30 (s, 1H). MS m/z (%): 394 (MH+, 58%), 259 (95%), 176 (58%), 130 (57%), 98 (51%), 84 (100%).

3-[1-(6-Chloro-1-indanylmethyl)-1,2,3,6-tetrahydropyridin-4-yl]-5-fluoro-]1H-indole hemifumarate, 6h.

Prepared from compound 3e. Mp 211–213° C. $^1$H NMR (DMSO-d$_6$) d 1.75–1.85 (m, 1H), 2.20–2.30 (m, 1H), 2.55–2.65 (m, 3H), 2.75–2.90 (m, 5H), 3.25 (broad s, 2H), 3.45 (p, 1H), 6.10 (broad s, 1H), 6.60 (s, 1H), 6.95 (t, 1H), 7.20 (d, 1H), 7.25 (d, 1H), 7.35 (dd, 1H), 7.40 (s, 1H), 7.45 (s, 1H), 7.55 (D, 1H), 11.25 (S, 1H). MS m/z (%): 381 (MH+, 5%), 167 (32%), 165 (100%), 130 (53%).

3-[1-(6-Chloro-1-indanylmethyl)-piperidin-4-yl]-5-fluoro-1H-indole fumarate, 6i.

Mp 214–216° C. $^1$H NMR (DMSO-d$_6$) d 1.75–1.85 (m, 3H), 2.00 (d, 2H), 2.25–2.30 (m, 1H), 2.40 (t, 2H), 2.60 (t,

1H), 2.75–2.90 (m, 4H), 3.20 (broad t, 2H), 3.45 (p, 1H), 6.60 (s, 2H), 6.90 (t, 1H), 7.15–7.25 (m, 3H), 7.30–7.35 (m, 2H), 7.45 (s, 1H), 10.90 (s, 1H). MS m/z (%): 383 (MH+, 16%), 248 (19%), 167 (31%), 165 (100%).

EXAMPLE 7

6-Chloro-3-[1-[2-(indan-1-yl)methylcarbonyl]-1,2,3,6-tetrahydropyridin-4-yl]-1H-indole, 7a A solution of indan-1-acetic acid (Anderson, A. G. et al; J. Org. Chem. 1989, 38(8), 1439–1444) (7.0 g, 39.7 mmol), DMF (3 ml) and $SOCl_2$ (17.5 g, 147 mmol) in $CH_2Cl_2$ (250 ml) was refluxed for 4 h. The mixture was evaporated and re-evaporated from toluene to give the corresponding acid chloride. To a solution of 6-chloro-3-(1,2,3,6-tetrahydropyridine-4-yl)-1H-indole (EP Patent publication No 465398-A1) (9.2 g, 39.7 mmol) and TEA (10 ml) in THF (120 ml) was added drop-wise over 20 min. a solution of the acid chloride in THF (120 ml). The mixture was stirred for 1.5 h and evaporated. $H_2O$ (50 ml) was added to the remanence and the mixture was extracted with $CH_2Cl_2$ (2×150 ml). After washing with $H_2O$ (20 ml) and brine (20 ml), the combined organic phases were dried with $MgSO_4$ and evaporated. The product was purified by column chromatography (EtOAc:heptane=1:1) to give the title compound 7a (7.8 g, 50%): $^1$H NMR (DMSO-$d_6$) δ1.55–1.72 (1H, m), 2.20–2.60 (3H, m), 2.69–2.95 (4H, m), 3.48–3.58 (1H, m), 3.61–3.81 (2H, m), 4.18 (2H, bs), 6.12 (1H, d), 7.05 (1H, dd), 7.08–7.16 (2H, m), 7.42 (1H, d), 7.49 (1H, dd), 7.81 (1H, dd), 11.31 (1H, bs).

EXAMPLE 8

6-Chloro-3-[1-[2-(indan-1-yl)ethyl]-1,2,3,6-tetrahydropyridine-4-yl]-1H-indole 8a To a suspension of $LiAlH_4$ (2.3 g, 60.0 mmol) in THF (150 ml) was added drop-wise over 20 min. to a solution of 6-Chloro-3-[1-[2-(indane-1-yl)methylcarbonyl]-1,2,3,6-tetrahydropyridine-4-yl]-1H-indole, 7a (7.8 g, 20.0 mmol) in THF (150 ml). The mixture was refluxed for 1.5 h and then cooled to 10–15° C. After drop-wise addition of $H_2O$ (3 ml), aqueous (15%) NaOH (3 ml) and $H_2O$ (12 ml), the solution was filtered and evaporated to almost dryness. The remanence was dissolved in $CH_2Cl_2$ and after drying with $MgSO_4$, the solution was evaporated to give the title compound 8a (5.7 g, 77%): mp 181–183° C., $^1$H NMR (DMSO-$d_6$) d 1.45–1.70 (2H, m), 1.95–2.15 (1H, m), 2.20–2.35 (1H, m), 2.45–2.60 (4H, m) 2.60–2.95 (4H, m), 3.00–3.20 (3H, m), 6.10–6.15 (1H, m), 7.00 (1H, dd), 7.10–7.25 (4H, m), 7.40 (2H, d), 7.80 (1H, d), 11.25 (1H, bs). MS m/z (%): 377 (MH+, 38%), 131 (100%).

The following compounds were prepared analogously according the procedures described in example 7 and 8:

5-Fluoro-3-[1-[2-(indan-1-yl)ethyl]-1,2,3,6-tetrahydropyridin-4-yl]-1H-indole, 8b.

Mp 172–176° C., $^1$H NMR (CDCl$_3$) d 1.70–1.80 (m, 2H), 2.15–2.25 (m, 1H), 2.30–2.40 (m, 1H), 2.60–2.70 (m, 4H), 2.75–2.85 (m, 2H), 2.85–2.90 (m, 1H), 2.90–3.00 (m, 1H), 3.20–3.30 (m, 3H), 6.10 (broad s, 1H), 6.95 (t, 1H), 7.15–7.30 (m, 6H), 7.50 (d, 1H), 8.15 (broad s, 1H). MS m/z(%): 361 (MH$^+$, 67%), 174 (74%), 131 (100%).

By hydrogenation of compound 8b at 3 atm in acetic acid using $PtO_2$ as catalyst in a Parr apparatus 5-fluoro-3-[1-[2-(indan-1-yl)ethyl]-piperidin-4-yl]-1H-indole, oxalate 8c was obtained. Mp 107–115. $^1$H NMR (DMSO-$d_6$) 1.55–1.85 (m, 2H), 1.90–2.00 (m, 2H), 2.10 (broad d, 2H), 2.20–2.30 (m, 2H), 2.75–2.85 (m, 1H), 2.85–2.95 (m, 1H), 3.00–3.20 (m, 6H), 3.55 (broad s, 2H), 6.90 (t, 1H), 7.15–7.20 (m, 2H), 7.20–7.25 (m, 2H), 7.25 (d, 1H), 7.30–7.40 (m, 1H), 7.35 (d, 1H), 11.00 (s, 1H). MS m/z (%): 363 (MH+, 9%), 117 (10%), 98 (100%).

5-Fluoro-3-[1-[4-(indan-1-yl)butan-1-yl]-1,2,3,6-tetrahydropyridin-4-yl]-1H-indole, 8d.

Mp 172–176° C., $^1$H NMR (CDCl$_3$) d 1.40–1.70 (m, 6H), 1.85–1.95 (m, 1H) 2.25–2.35 (m, 1H), 2.50 (t, 2H), 2.60 (broad s, 2H), 2.70 (t, 2H), 2.80–2.90 (m, 1H), 2.90–3.00 (m, 1H), 3.05–3.15 (m, 1H), 3.25 (broad s, 2H), 6.10 (broad s, 1H), 6.95 (t, 1H), 7.10–7.30 (m, 6H), 7.50 (d, 1H), 8.10 (s, 1H). MS m/z(%): 389 (MH$^+$, 9%), 202 (100%), 171 (44%), 129 (73%).

By hydrogenation of compound 8d at 3 atm in acetic acid using $PtO_2$ as catalyst in a Parr apparatus 5-fluoro-3-[1-[4-(indan-1-yl)butan-1-yl]-piperidin-4-yl]-1H-indole 8e was obtained. Mp 83–86° C., $^1$H NMR (CDCl$_3$) d 1.25–1.90 (m, 9H), 1.95–2.10 (m, 4H), 2.20–2.30 (m, 1H), 2.35–2.45 (m, 2H), 2.70–2.90 (m, 3H), 3.05–3.15 (m, 3H), 6.90 (t, 1H), 6.95 (s, 1H), 7.10–7.30 (m, 6H), 8.15 (s, 1H). MS m/z(%): 391 (MH$^+$, 61%), 256 (78%), 98 (100%).

6-Chloro-3-[1-[4-(indan-1-yl)butan-1-yl)-piperidin-4-yl]-1H-indole, oxalate 8f.

Mp 206–208° C. $^1$H NMR (DMSO-$d_6$) d 1.40–1.50 (m, 3H), 1.60–1.65 (m, 1H), 1.65–1.70 (m, 2H), 1.80–1.90 (m, 1H), 1.95–2.10 (m, 4H), 2.20–2.30 (m, 1H), 2.70–2.80 (m, 1H), 2.80–2.90 (m, 1H), 2.95–3.10 (m, 6H), 3.55 (broad d, 2H), 6.95 (d, 1H), 7.10–7.30 (m, 5H), 7.40 (s, 1H), 7.65 (d, 1H), 11.10 (s, 1H). MS m/z (%): 407 (MH+, 69%), 256 (100%), 117 (39%), 98 (51%).

6-Chloro-3-[1-[3-(indan-1-yl)propan-1-yl]-1,2,3,6-tetrahydropyridin-4-yl]-1H-indole, 8g.

Mp 198–200° C., $^1$H NMR (CHCl$_3$-d) d 1.40–1.55 (1H, m), 1.60–1.80 (3H, m), 1.75–1.95 (1H, m), 2.20–2.40 (1H, m), 2.45–2.60 (4H, m), 2.70 (2H, t), 2.80–3.00 (2H, m), 3.10–3.15 (1H, m), 3.20–3.25 (2H, m), 6.15 (1H, s), 7.05–7.30 (6H, m), 7.30 (1H, d), 7.80 (1H, d), 8.25 (1H, bs). MS m/z (%): 3.91 (MH+, 5%), 157 (100%), 129 (76%), 188 (56%).

6-Chloro-3-[1-[4-(indane-1-yl)butan-1-yl]-1,2,3,6-tetrahydropyridin-4-yl-1H-indole oxalate, 8h.

Mp 191–192° C., $^1$H NMR (DMSO-$d_6$) d 1.40–1.50 (3H, m), 1.60–1.65 (1H, m), 1.70–1.80 (2H, m), 1.80–1.90 (1H, m), 2.30–2.25 (1H, m), 2.25–2.30 (3H, m), 2.30–2.90 (1H, m), 3.05–3.20 (3H, m), 3.35 (2H, bs), 3.80 (2H, bs), 6.10 (1H, s), 7.10 (1H, d), 7.10 (2H,m), 7.20 (2H, m), 7.45 (1H, s), 7.55 (11H, s), 7.80 (1H, d). MS m/z (%): 405 (MH+, 6%), 202 (100%), 129 (54%), 171 (36%).

The synthesis of 3-(indan-1-yl)propanoic and acid 4-(indan-1-yl)butanoic acid is described by A. Mukhopadhyay et al. *J. Indian Chem. Soc.* 1985, 62(9), 690–2.

EXAMPLE 9

Indane-2-carboxylic Acid 9a (Intermediate)

A solution of indane-2,2-dicarboxylic acid (17 g, Baeyer and Perkin, *Ber.* 1884, 17, 122) in NMP (200 ml) was heated to 150° C. for 1 hour. After cooling to 20° C. the solution was poured in water (300 ml) and concentrated hydrochloric acid was added to pH=1. Conventional work up with ether gave the title product (4.7 g). Mp 132–33° C. (from ether).

EXAMPLE 10

6-Chloro-3-[1-[(indan-2-yl)carbonyl]-1,2,3,6-tetrahydopyrid-4-yl]-1H-indole, 10a To a solution of 9a (2.1 g) in dichloromethane (200 ml) was added thionyl chloride (1.4 ml) and DMF (2 ml). After reflux for 2.5 hours, the mixture was concentrated in vacuo and dissolved in DMF (50 ml). The solution was added drop-wise to an ice-cooled solution of 6-chloro-3-(1,2,3,6-tetrahydropyridin-4-yl)-1H-indole (EP Patent publication No 465398-A1) (3.0 g) in DMF (200 ml) and triethylamine (9 ml). The reaction mixture was left with stirring at room temperature for 16 hours and then poured into a saturated solution of sodium chloride (500 ml). Conventional work up with ethyl acetate gave the title product (4.7 g) which was sufficiently pure for further reaction.

In a similar manner the following compounds were prepared:

3-[1-[(Indan-2-yl)carbonyl]-1,2,3,6-tetrahydopyrid-4-yl]-1H-indole, 10b.
Prepared from compound 9a and 3-(1,2,3,6-tetrahydropyridin-4-yl)-1H-indole.

7-Chloro-3-[1-[(indan-2-yl)carbonyl]-1,2,3,6-tetrahydopyrid-4-yl]-1H-indole, 10c.
Prepared from 9a and 7-chloro-3-(1,2,3,6-tetrahydropyridin-4-yl)-1H-indole.

6,7-Dihloro-3-[1-[(indan-2-yl)carbonyl]-1,2,3,6-tetrahydopyrid-4-yl]-1H-indole, 10d.
Prepared from 9a and 6,7-dichloro-3-(1,2,3,6-tetrahydropyridin-4-yl)-1H-indole.

3-[1-[(Indan-2-yl)carbonyl]-1,2,3,6-tetrahydopyrid-4-yl]-5,6-methylenedioxy-1H-indole, 10e.
Prepared from 9a and 5,6-methylenedioxy-3-(1,2,3,6-tetrahydropyridin-4-yl)-1H-indole.

5-[4-[(Indan-2-yl)carbonyl]piperazin-1-yl]-1H-indole, 10f.
Prepared from 9a and 5-(piperazinyl)-1H-indole.

6-Chloro-3-[1-[2-(indan-2-yl)methylcarbonyl]-1,2,3,6-tetrahydopyrid-4-yl]-1H-indole, 10g.
From 2-(indan-2-yl)acetic acid and 6-chloro-3-(1,2,3,6-tetrahydropyridin-4-yl)-1H-indole.

6-Chloro-3-[1-[3-(indan-2-yl)ethylcarbonyl]-1,2,3,6-tetrahydopyrid-4-yl]-1H -indole, 10h.
From 3-(indan-2-yl)propionic acid 6-chloro-3-(1,2,3,6-tetrahydropyridin-4-yl)-1H-indole.

6-Chloro-3-[1-[4-(indan-2-yl)propylcarbonyl]-1,2,3,6-tetrahydopyrid-4-yl]-1H-indole, 10i.
From 4-(indan-2-yl)butyric acid 6-chloro-3-(1,2,3,6-tetrahydropyridin-4-yl)-1H-indole.

EXAMPLE 11

6-Chloro-3-[1-(indan-2-yl)methyl-1,2,3,6-tetrahydropyridin-4-yl]-1H-indole,oxalate 11a A solution of of 10a (3.2 g) in THF (100 ml) was added to a cooled suspension of LiAlH4 (0.9 g) in THF (150 ml) at 5° C. The mixture was stirred at room temperature for 4 hours. The mixture was then cooled on ice and after drop-wise addition of water (1.5 ml), 15% NaOH (1 ml), and water (3.5 ml) it was filtered and evaporated in vacuo. The residue was dissolved in $CH_2Cl_2$ and worked up in a conventional manner yielding yellow crystals (3.2 g) which were recrystallized from actone giving 1.1 g, mp 161–63° C. The title oxalate was crystallized from acetone. Yield 0.45 g, mp. 203–5° C. $^1$H NMR (DMSO-$d_6$) d 2.65–2.80 (m, 5H), 2.80–2.95 (m, 1H), 2.95–3.30 (m, 5H), 3.65 (s, 2H), 6.15 (s, 1H), 7.05 (dd, 1H), 7.10–7.15 (m, 2H), 7.15–7.25 (m, 2H), 7.45 (d, 1H), 7.55 (d, 1H), 7.85 (d, 1H), 11.45 (s, 1H). MS m/z (%): 363 (MH+, 100%), 245 (17%), 230 (20%).

In a similar manner the following compounds were prepared:

3-[1-(Indan-2-yl)methyl-1,2,3,6-tetrahydropyridin-4-yl]-1H-indole 11b. Prepared from 10b.
Mp 156–157° C. $^1$H NMR (DMSO-$d_6$) δ2.40 (d, 2H), 2.45–2.85 (m, 7H), 2.90–3.10 (m, 2H), 3.15 (d, 2H), 6.15 (s, 1H), 6.95–7.25 (m, 6H), 7.30–7.40 (m, 2H), 7.80 (d, 1H), 11.10 (s, 1H). MS m/z (%): 329 (MH+, 84%), 160 (87%), 131 (100%).

7-Chloro-3-[1-(indan-2-yl)methyl-1,2,3,6-tetrahydropyridin-4-yl]-1H-indole, oxalate 11c.
Prepared from 10c. Mp 135–136° C. $^1$H NMR (DMSO-$d_6$) δ2.70–3.05 (m, 5H), 3.05–3.20 (m, 2H), 3.30 (d, 2H), 3.40 (t, 2H), 3.90 (s, 2H), 6.20 (s, 1H), 7.05–7.30 (m, 6H), 7.60 (d, 1H), 7.85 (d, 1H), 11.75 (s, 1H). MS m/z (%): 365, 363 (MH+, 46%, 81%), 160 (100%), 131 (53%), 98 (81%).

6,7-Dichloro-3-[1-(indan-2-yl)methyl-1,2,3,6-tetrahydropyridin-4-yl]-1H-indole, 11d.
Prepared form 10d. Mp 151–152° C. $^1$H NMR (CDCl$_3$) δ2.45–2.65 (m, 4H), 2.65–2.90 (m, 5H), 3.00–3.20 (m, 2H), 3.20–3.30 (m, 2H), 6.15 (broad s, 1H), 7.05–7.30 (m, 6H), 7.70 (d, 1H), 8.35 (broad s, 1H). 399, 397 (MH+, 33%, 53%), 160 (100%), 131 (24%).

3-[1-(Indan-2-yl)methyl-1,2,3,6-tetrahydropyridin-4-yl]-5,6-methylenedioxy-1H-indole, 11e.
Prepared from 10 e.Mp 192–193° C. $^1$H NMR (DMSO-$d_6$) δ2.40 (d, 2H), 2.45–2.55 (m, 2H), 2.55–2.80 (m, 5H), 2.95–3.05 (m, 2H), 3.15 (s, 2H), 5.95 (s, 2H), 6.00 (s, 1H), 6.90 (s, 1H), 7.05–7.15 (m, 2H), 7.15–7.20 (m, 3H), 7.25 (s, 1H), 11.90 (s. 1H). MS m/z (%): 373 (MH+, 100%), 160 (100%), 131 (73%), 114 (80%).

5-[4-(Indan-2-yl)methylpiperazin-1-yl]-1H-indole, dihydrochloride 11f. Prepared form 10f.
Mp 263–265° C. $^1$H NMR (DMSO-$d_6$) δ2.80–2.90 (m, 2H), 2.90–3.05 (m, 1H), 3.05–3.25 (m, 2H), 3.40 (d, 2H), 3.45–3.95 (m, 8H), 6.45 (s, 1H), 7.05–7.25 (m, 5H), 7.35–7.65 (m, 3H), 11.25 (s, 1H). MS m/z (%): 332 (MH+, 31%), 159 (100%), 131 (72%).

6-Chloro-3-[1-[2-(indan-2-yl)ethyl]-1,2,3,6-tetrahydropyridin-4-yl]-1H-indole, 11g.
Prepared form 10g. Mp 217–218° C. $^1$H NMR (DMSO-$d_6$) δ1.70 (q, 2H), 2.35–2.70 (m, 9H), 2.90–3.20 (m, 4H), 6.10 (broad s, 1H), 6.95–7.25 (m, 5H), 7.40 (d, 2H), 7.80 (d, 1H), 11.25 (broad s, 1H). MS m/z (%): 379, 377 (MH+, 7%, 16%), 174 (93%), 143 (100%).

6-Chloro-3-[1-[3-(indan-2-yl)propan-1-yl]-1,2,3,6-tetrahydropyridin-4-yl]-1H-indole, 11h
Prepared form 10h. Mp 176–177° C. $^1$H NMR (DMSO-$d_6$) δ1.40–1.70 (m, 4H), 2.30–2.70 (m, 9H), 2.90–3.15 (m, 4H), 6.10 (broad s, 1H), 6.95–7.25 (m, 5H), 7.40 (d, 2H), 7.80 (d, 1H), 11.25 (broad s, 1H). MS m/z (%): 391 (MH+, 6%), 188 (100%), 129 (47%).

6-Chloro-3-[1-[4-(indan-2-yl)butan-1-yl]-1,2,3,6-tetrahydropyridin-4-yl]-1H-indole, 11i
Prepared from 10i. Mp 211–214° C. $^1$H NMR (DMSO-$d_6$) δ1.30–1.65 (m, 6H), 2.25–2.70 (m, 9H), 2.90–3.15 (m, 4H), 6.10 (broad s, 1H), 6.95–7.25 (m, 5H), 7.40 (d, 2H), 7.80 (d, 1H), 11.25 (broad s, 1H). MS m/z (%): 407, 405 (MH+, 4%, 10%), 202 (100%), 129 (93%).

With compound 40a as starting material following the procedures in Examples 10 and 11 the following compound was prepared:

6-chloro-3-[1-[(4-(2-Propyl)oxyindan-2-yl)methyl] piperidin-4-yl]-1H-indole,oxalate, 11j,
Mp 119–126° C. $^1$H NMR (DMSO-$d_6$): d 1.26 (3H, d). 1.27 (3H, d), 1.95–2.2 (4H, m), 2.60 (1H, dd), 2.74 (1H, dd), 2.91 (1H, quin), 3.0–3.2 (5H, m), 3.2–3.3 (2H, m), 3.5–3.7 (2H, m), 4.57 (1H, h), 6.77 (2H, t), 7.0 (1H, dd), 7.09 (1H, t), 7.20 (1H, s), 7.41 (1H, s), 7.66 (1H, d). MS m/z (%): 423 (MH+, 59%), 249 (21%), 147 (20%), 98 (100%).

5-Fluoro-3-[1-[(4-(2-propyl)oxyindan-2-yl)methyl]piperid-4-yl]-1H-indole, oxalate, 11k, mp 181–189° C. $^1$H NMR (DMSO-d$_6$): d 1.26 (3H, d), 1.26 (3H, d), 2.61 (1H, dd), 2.74 (1H, dd), 2.7–2.8 (2H, m), 2.92 (1H, h), 3.0–3.2 (2H, m), 3.15–3.3 (2H, m), 3.3–3.45 (2H, m), 3.7–3.9 (2H, m), 4.57 (1H, h), 6.11 (1H, s), 6.76 (1H, d), 6.79 (1H, d), 6.99 (1H, dt), 7.42 (1H, dd), 7.5–7.65 (2H, m). MS m/z (%): 405 (MH+, 7%), 231 (4%), 147 (5%), 98 (9%), 44 (100%).

With compound 40b as starting material following the procedures in Examples 10 and 11 the following compound was prepared:

6-Chloro-3-[1-[(5,6-dimethoxyindan-2-yl)methyl]piperid-4-yl]-1H-indole, 11l, mp 68–79° C. $^1$H NMR (DMSO-d$_6$): d 1.68 (2H, dq), 1.91 (2H, ddd), 2.06 (2H, dt), 2.31 (2H, d), 2.58 (2H, dd). 2.65–2.77 (2H, m), 2.91 (1H , dd), 3.70 (6H. s), 6.80 (2H, s), 6.96 (1H, dd), 7.15 (1H, d), 7.36 (1H, d), 7.54 (1H, d), 10.91 (1H, s). MS m/z (%): 425 (MH+, 7%), 249 (11%), 191 (16%), 98 (100%).

EXAMPLE 12

4-Methyl-1-indanone-3-carboxylic acid, 12a (Intermediate)

To a mixture of o-tolualdehyde (500 g), ethyl cyanoacetate (445 g) and ethanol (500 ml) was added piperidine (16 ml). After azeotrope destillation (200 ml) more ethanol (200 ml) was added, and the mixture was refluxed for 2 hours. The solution was cooled to 40° C., and a solution of NaCN (225 g) in water (300 ml) was added over 20 minutes. The mixture was stirred for one hour and was then left for 16 hours at room temperature. Concentrated HCl (5 l) was added slowly and then water/ethanol was destilled off until the temperature reached 100° C. The mixture was then refluxed for 4 hours and then stirred at room temperature for 16 hours. The mixture was filtered, and the crystals were washed with water. The crystals were dissolved in 4 M NaOH (3 l) and filtrated. Then pH was adjusted to 1 with concentrated hydrochloric acid, and the crystals were filtered off and dried yielding 610 g which was dissolved in thionyl chloride (2 l). DMF (10 ml) was added and the solution was refluxed for 2.5 hours and evaporated in vacuo. The residue was dissolved in CH$_2$Cl$_2$ (1.2 l) and was added during 1 hour to a cooled mixture of AlCl$_3$ (600 g) in CH$_2$Cl$_2$ (4 l) at 0–5° C. The mixture was stirred at room temperature for 16 hours and was then poured on ice/water (5 l) and concentrated hydrochloric acid (500 ml). Conventional work up gave the crude title product (605 g), which was purified by column chromatography on silica gel eluted with CH$_2$Cl$_2$-ether-acetic acid (50:50:2) giving 236 g of the title product.

EXAMPLE 13

7-Methyl-indane-1-carboxylic acid, 13a (Intermediate)

To a solution of 12a (100 g) in trifluoroacetic acid is added trietylsilane (141 g). The mixture was stirred for 72 hours at room temperature and was then evaporated in vacuo the residue was dissolved in ethyl acetate and was extracted with dilute NaOH solution. The aqueous phase was washed with etyl acetate and was then acidified with concentrated hydrochloric acid. Conventional work up with ethyl acetate gave 80.4 g of crude product. Purification on silica gel eluted with ethyl acetate-heptane-acetic acid gave the title compound (76.6 g).

EXAMPLE 14

3,6,7,8-Tetrahydrocyclopent[e]indole-8-carboxylic acid, 14a (Intermediate)

A solution of 13a (61.2 g) in CH$_2$Cl$_2$ (100 ml) was added with stirring during 20 minutes at −50° C. to a mixture of concentrated nitric acid (150 ml) and CH$_2$Cl$_2$ (40 ml). After stirring at −52° C. for 30 minutes the mixture was poured on ice and saturated NaCl solution. Conventional work up with ethyl acetate gave 58.2 g of crude product which was purified on silica gel eluted with heptane-ethyl acetate (2:1) to give 45.6 g of product containing 32% of 5-nitro compound together with other nitro compounds. This product was dissolved in DMF (200 ml) and was heated to 88° C. Tris-(dimethylamino)methane (34.5 g) was added, and the temperature was raised to 123° C., and the mixture was stirred for 2 hours. The mixture was cooled to 27° C., and a solution of semicarbazid, HCl (19 g) in water (200 ml) was added over 8 minutes. The mixture was then stirred for 70 minutes at room temperature. Ethanol (500 ml) was added and iron powder (30 g) and acetic acid (120 ml) was added in portions at 50° C. After reflux for 45 minutes the mixture was filtered and concentrated to 500 ml in vacuo. Water was added and the mixture was worked up with ethyl acetate. The residue was purified on silica gel eluted with ethyl acetate, giving 5.7 g of the title product. Mp 166–7° C.

EXAMPLE 15

8-[4-(6-Chloro-1H-indol-3-yl)-1,2,3,6-tetrahydropyridin-1-ylcarbonyl]-3,6,7,8-tetrahydrocyclopent[e]indole, 15a A solution of 14a (1.4 g), 6-chloro-3-(1,2,3,6-tetrahydropyridin-4-yl)-1-H-indole (1.6 g), dicyclohexylcarbodiimid (1.9 g), and 4-dimethylaminopyridine (0.1 g) in THF (100 ml) was stirred for 24 hours at room temperature. The mixture was filtered and evaporated in vacuo. The residue was purified on silica gel eluted with ethyl acetate-heptane (3:2) giving 1.1 g of the title product as an amorpheous powder.

EXAMPLE 16

8-[4-(6-Chloro-1H-indol-3-yl)-1,2,3,6-tetrahydropyridin-1-ylmethyl]-3,6,7,8-tetrahydro-cyclopent[e]indole, oxalate 16a The title product was prepared from 15a (1.05 g) as described in Example 3. Yield 0.59 g, mp 155–7° C. $^1$H NMR (DMSO-d$_6$) δ2.10–2.40 (m, 2H), 2.75–2.95 (m, 3H), 2.95–3.25 (m, 2H), 3.35–3.65 (m, 3H), 3.85–4.10 (m, 3H), 6.15 (s, 1H), 6.50 (s, 1H), 6.95 (d, 1H), 7.10 (dd, 1H), 7.25 (d, 1H), 7.35 (t, 1H), 7.45 (d, 1H), 7.55 (d, 1H), 7.85 (d, 1H), 11.15 (s, 1H), 11.55 (s, 1H). MS m/z (%): 402 (MH+, 6%), 170 (96%), 156 (100%).

EXAMPLE 17

4-nitroindane-2-carboxylic acid chloride, 17a (Intermediate)

A mixture of 3-nitro-o-xylene (100 g), N-bromosuccinimide, and dibenzoylperoxide (2 g) was heated to reflux for 14 hours. The mixture was filtered and evaporated in vacuo to give an oil (202 g) which was purified on silica gel eluted with heptane-ether (10:1) giving 86.4 of bromo compound which was dissolved in NMP (850 ml) and added to a mixture of diethyl malonate (38 g) and 30% Na-methanolate in methanol (105 ml) in NMP (1 l) at 53–60° C. After stirring for 30 minutes at 60° C., the mixture was cooled, poured in cold water, and was worked up with a mixture of ether and ethyl acetate. The residue was purified on silica gel eluted with toluene-ethyl acetate (6:1). The product (25.1 g) was dissolved in ethanol (250 ml) and THF (50 ml). KOH (27 g) in water (150 ml) was added, and the mixture was stirred for 16 hours at room temperature. The mixture was concentrated in vacuo to 100 ml and was filtered through activated carbon. The filtrate was acidified with concentrated hydrochloric acid and was worked up with a mixture of ether and ethyl acetate. The residue (16.46 g) was dissolved in NMP (150 ml) and was heated to 145° C. for 10 minutes. The solution was cooled to room temperature and was poured in saturated NaCl solution. Work up with ether/ethyl acetate in a usual manner gave 10.7 g of solid of which 6.0 g was dissolved in $CH_2C_2$ (100 ml) and DMF (1 ml). Thionyl chloride (8.4 ml) was added, and the solution was refluxed for 16 hours. Evaporation in vacuo gave the semi-crystalline title compound (8.4 g).

5-Nitroindane-2-carboxylic acid chloride, 17b

A solution of indane-2-carboxylic Acid 9a (18.8 g) in ether (250 ml) was added to conc. sulfuric acid (300 ml) (temp.=3–13° C.). To this mixture, a solution of conc. nitric acid (4.4 ml) and conc. sulfuric acid (100 ml) was added (temp.=−1° C.). The mixture was stirred at 2–8° C. for 1 h, poured onto ice, and the aqueous phase was extracted with ether. The combined organic extracts were washed with brine, dried ($MgSO_4$) and evaporated to dryness in vacuo. The residue was crystallized from ether to give 5-nitroindane-2-carboxylic acid (6.0 g). The solid was dissolved in $CH_2Cl_2$ (100 ml) and DMF (1 ml). Thionyl chloride (8.4 ml) was added, and the solution was boiled under reflux for 5 hours. Evaporation in vacuo gave the title compound (8.6 g).

EXAMPLE 18

6-Chloro-3-[1-(4-acetylaminoindan-2-yl)methyl-1,2,3,6-tetrahydropyridine-4-yl]-1H-indole, oxalate 18a To a solution of 6-chloro-3-(1,2,3,6-tetrahydropyridin-4-yl)-1-H-indole (6.4 g) in DMF (250 ml) and triethylamine (14 g) was added a solution of 17a (8.4 g) in DMF (50 ml) during 25 minutes at 3–5° C. The mixture was then stirred for 45 minutes at room temperature and then poured in water. The precipitate was filtered off, washed with water and dried to give 9.11 g of solid, which was slurried in refluxing 90% ethanol (450 ml). Iron powder (9 g) and concentrated hydrochloric acid (1.8 ml) was added in portions during 15 minutes, and the mixture was refluxed for another hour. The mixture was concentrated in vacuo, and ice and concentrated ammonium hydroxide was added. Conventional work up with ethyl acetate gave 4.67 g, which was treated with $LiAlH_4$ as described in Example 11 giving 3.2 g solid of which 2 g was dissolved in THF (50 ml) and triethylamine (3.5 ml). To the ice cooled solution a solution of acetyl chloride (0.43 g) in THF (15 ml) was added at 1–4° C. After warm up to room temperature the mixture was filtered and evaporated in vacuo, and the residue was purified on silica gel eluted with ethyl acetate-ethanol-triethylamine (100:4:4) giving 1.51 g, from which the title product was crystallized as the oxalate salt from 2-propanol. Yield 1.29 g, mp 143–4° C. $^1$H NMR (DMSO-$d_6$) δ2.0 (s, 3H), 2.55–3.00 (m, 5H), 3.00–3.15 (m, 4H), 3.25 (broad s, 2H), 3.70 (s, 2H), 6.15 (s, 1H), 7.0 (d, 1H), 7.05–7.15 (m, 2H), 7.35 (d, 1H), 7.45 (d, 1H), 7.55 (d, 1H), 7.85 (d, 1H), 9.40 (s, 1H), 11.45 (s, 1H). MS m/z (%): 420 (MH+, 11%), 217 (87%), 174 (100%).

In a similar manner the following compound was prepared:
6-Chloro-3-[1-(4-acetylaminoindan-2-yl)methylpiperidin-4-yl]-1H-indole,oxalate, 18b.

From 6-chloro-3-(piperidine-4-yl)-1H-indole and 17a.
Mp 153–5° C. $^1$H NMR (DMSO-$d_6$) δ1.80–2.10 (m, 7H), 2.55–3.15 (m, 10H), 3.40 (broad d, 2H), 6.95–7.05 (m, 2H), 7.10 (t, 1H), 7.20 (d, 1H), 7.35–7.40 (m, 2H), 7.60 (d, 1H), 9.35 (s, 1H), 11.05 (s, 1H). MS m/z (%): 422 (MH+, 100%), 249 (2%), 98 (16%).

The appropriate w-(6-acetylamino-1-indanyl)-alkanoic acids were converted to the corresponding acid chloride as described in Example 17, and reacted as described in Example 18 with 6-Chloro-3-(1,2,3,6-tetrahydropyridin-4-yl)-1H-indole to give the following compounds:

6-Chloro-3-1-[2-(6-acetylaminoindan-1-yl)ethyl]-1,2,3,6-tetrahydropyridin-4-yl]-1H-indole oxalate, 18c.

Mp 153–155° C., $^1$H NMR (DMSO-$d_6$) d 1.60–1.90 (2H, m), 2.00 (3H, s), 2.10–2.35 (2H, m), 2.65–2.90 (4H, m), 3.05–3.30 (3H, m), 3.30–3.50 (2H, m), 3.90 (2H, bs), 6.10 (1H, s), 7.05–7.15 (2H, m), 7.25 (2H, d), 7.45 (1H, s), 7.60 (2H, m), 7.85 (1H, d), 9.90 (1H, bs), 11.50 (1H, bs). MS m/z (%): 434 (MH+, 3%), 188 (100%), 231 (14%), 174 (12%).

6-Chloro-3-[1-[3-(6-acetylaminoindan-1-yl)propan-1-yl]-1,2,3,6-tetrahydropyridin-4-yl]-1H-indole oxalate, 18d.

Mp 110–115° C., $^1$H NMR (DMSO-$d_6$) d 1.35–1.50 (1H, m), 1.60–1.70 (1H, m), 1.80 (3H, bs), 2.00 (3H, s), 2.20–2.39 (1H, m), 2.65–2.90 (4H, m), 3.05–3.20 (3H, m), 3.90 (2H, bs), 3.80 (2H, bs), 6.10 (1H, s), 7.05–7.10 (2H, m), 7.25 (2H, d), 7.45 (1H, s), 7.55 (1H, d), 7.80 (1H, d), 9.80 (1H, bs), 11.50 (1H, bs). MS m/z (%): 448 (MH+, 5%), 245 (100%), 214 (35%), 246 (16%).

6-Chloro-3-[1-[4-(6-acetylaminoindan-1-yl)butan-1-yl]-1,2,3,6-tetrahydropyridin-4-yl]-1H-indole oxalate, 18e.

Mp 125–128° C., $^1$H NMR (DMSO-$d_6$) d 1.25–1.50 (3H, m), 1.50–1.90 (4H, m), 2.00 (3H, s), 2.10–2.30 (1H, m), 2.60–2.90 (4H, m), 2.90–3.15 (3H, m), 3.40 (2H, bs), 3.80 (2H, bs), 6.10 (1H, s ), 7.00–7.10 (2H, m), 7.25 (1H, d), 7.45 (1H, s), 7.55 (1H, d), 7.80 (1H, d), 9.85 (1H, bs), 11.50 (1H, bs). MS m/z (%): 462 (MH+, 4%), 259 (100%), 186 (43%), 228 (17%).

2-(6-acetylaminoindan-1-yl)acetic acid, 3-(6-acetylaminoindan-1-yl)propanoic acid and 4-(6-acetylaminoindan-1-yl)butanoic acid were prepared from 6-nitro-1-indanecarboxylic acid by classical chain elongations by using KCN or diethyl malonate. The methodology is described for an analogous indane serie by R. Gruber et al. *Tetrahedron* 1974, 30, 3605–10. Alane was used for the reduction of the intermediate carboxylic acids.

3-[1-(5-Acetylaminoindan-2-yl)methyl-1,2,3,6-tetrahydropyridine-4-yl]-6-chloro-1H-indole, oxalate, 18f.

Prepared from 17b. Mp 201–203° C. $^1$H NMR (DMSO-$d_6$) d 2.00 (s, 3H), 2.55–3.20 (m, 11H), 3.55 (broad s, 2H), 6.15 (broad s, 1H), 7.00–7.15 (m, 2H), 7.25 (d, 1H), 7.45 (d, 1H), 7.50 (broad s, 2H), 7.85 (d, 1H), 9.80 (s, 1H), 11.40 (broad s, 1H). MS m/z (%): 420 (MH+, 5%), 217 (12%), 174 (100%).

3-[1-(5-Acetylaminoindan-2-yl)methylpiperidin-4-yl]-6-chloro-1H-indole, hemifumerate 18g.

Prepared from 17b. Mp 151–152° C. $^1$H NMR (DMSO-$d_6$) d 1.65–2.05 (m, 7H), 2.30 (t, 2H), 2.45–2.90 (m, 6H), 2.90–3.20 (m, 4H), 6.55 (s, 1H), 6.95 (dd, 1H), 7.10 (d, 1H), 7.15 (dd, 1H), 7.40 (d, 1H), 7.50 (s, 1H), 7.60 (d, 1H), 9.80 (s, 1H), 10.95 (broad s, 1H). MS m/z (%): 424, 422 (MH+, 19%, 54%), 249 (13%), 98 (100%).

EXAMPLE 19

1-Acetyl-2,3-dihydro-3-[2-(methanesulphonyl)ethyl]-1H-indole, 19a (Intermediate)

To a solution of indole-3-acetic acid (100 g) in methanol (1 l) was added ether saturated with HCl (200 ml), and the solution was left at room temperature for 3 hours. The solution as evaporated in vacuo, and the residue was dissolved in THF 1.2 l) and added slowly with cooling to a stirred suspension of $LiAlH_4$ (28.6 g) in THF (1 l). After stirring for 2 hours at room temperature, the mixture was cooled in an ice bath, and water (57 ml), 15% NaOH (29 ml), and water (143 ml) was added. The mixture was filtered and evaporated in vacuo, and the residue (84.9 g) was dissolved in dioxane (1.5 l). Borane trimethylamine complex (200 g) was added, and and to the stirred mixture was added concentrated hydrochloric acid (150 ml) during 1 hour. The mixture was heated to 40° C. for 30 minutes and then to reflux for 2.5 hours. Then 6 M hydrochloric acid (460 ml) was added and reflux was continued for 30 minutes. The solution was concentrated in vacuo, and the residue was poured on ice. The solution was washed with ether and was made basic with concentrated NaOH and then extracted with ether. The organic phase was dried over $MgSO_4$ and was evaporated in vacuo. The residue was dissolved in $CH_2Cl_2$ (680 ml) and triethylamine (68 ml). Acetyl chloride (36 ml) was added at 5° C. during 1 hour. After further stirring for 1 hour at room temperature, the mixture was washed with dilute hydrochloric acid, and $NaHCO_3$ solution. After drying over $MgSO_4$ and evaporation in vacuo, the residue was dissolved in methanol (500 ml), and 30% Na-methanolat (10 ml) was added. The mixture was stirred for 4 hours at room temperature and was then evaporated in vacuo and was dissolved in $CH_2Cl_2$ and was washed with saturated NaCl solution, dried over $MgSO_4$ and evaporation in vacuo. The residue (75.4 g) was dissolved in $CH_2Cl_2$ (1 l) and triethylamine (100 ml). With cooling was added a solution of methanesulphonic chloride (27 ml) in $CH_2Cl_2$ (175 ml) at 10° C. After stirring for 30 minutes at 0° C. and 1 hour at room temp the mixture was evaporated in vacuo and was purified on silica gel eluted with ethyl acetate to give the title product as an oil (74 g).

In a similar manner the following compounds were prepared:

1-Formyl-2,3-dihydro-3-[2-(methanesulphonyl)ethyl]-1H-indole, 19b.

Formylation was done with a mixture of formic acid and acetic acid anhydride. The compound was an oil.

1-Acetyl-5-bromo-2,3-dihydro-3-[2-(methanesulphonyl) ethyl]-1H-indole, 19c.

Bromination was done by treatment of 19a with bromine in a mixture of acetic acid and dichloromethane. The compound was an oil.

1-tert-Butoxycarbonyl-2,3-dihydro-3-[2-(methanesulphonyl)ethyl]-1H-indole, 19d tert-Butoxycarbonylation was done with di-tert-butyl dicarbonate. The compound was an oil.

1-tert-Butoxycarbonyl-2,3-dihydro-3-[4-(methanesulphonyl)butan-1-yl]-1H-indole, 19e.

From 4-(1H-indol-3-yl)butyric acid.

1-Acetyl-5-fluoro-2,3-dihydro-3-(2-bromoethyl)-1H-indole, 19f 5-fluoro-indole (15.0 g, 135.2 mmol) was dissolved in dry $Et_2O$ (450 ml) and cooled to 0° C. before a solution of oxalyl chloride in dry $Et_2O$ (50 ml) was added over 15 min. The mixture was stirred 30 min at 0° C. and 3 hours at room temperature. The crystals were collected by filtration and washed with $Et_2O$ to give 19.5 g of solid which was dissolved in EtOH (140 ml) and cooled to 0° C. before triethylamine (9.6 g) was added drop-wise. The mixture was refluxed for 3 hours and stirred at room temperature for 24 hours. The crystals were collected by filtration and washed with $H_2O$ and $Et_2O$ to give 18.0 g of solid which, after drying in a vacuum oven, was dissolved in dry THF (150 ml) and added drop-wise to a cooled suspension (5–15° C.) of $LiAlH_4$ (16.1 g) in dry THF (350 ml). The mixture was refluxed for 4 hours and cooled to 10° C. After drop-wise addition of $H_2O$ (16 ml), aqueous (15%) NaOH (16 ml) and $H_2O$ (80 ml), the solution was filtered and evaporated to almost dryness. The remanence was dissolved in EtOAc and dried with $MgSO_4$. Evaporation of the solvent gave the 2-(5-fluoroindol-3-yl)ethanol (15.2 g) as an oil, which was treated as described in Example 19, starting with the borane trimethylamine reduction followed by acylation, to give the mesylate of the title compound which was refluxed for 2 hours in acetone (200 ml) with LiBr (8.0 g). The mixture was cooled, filtered, evaporated and purified by column chromatography using EtOAc:heptane=1:2 as the eluent to give the title compound (9.0 g).

1-Acetyl-5-methyl-2,3-dihydro-3-(2-bromoethyl)-1H-indole, 19g Prepared in a similar manner as 19f.

EXAMPLE 20

3-[1-[2-(1-Acetyl-2,3-dihydro-1H-indol-3-yl)ethyl]-1,2,3,6-tetrahydropyridin-4-yl]-6-chloro-1H-indole, 20a A mixture of of 6-chloro-3-(1,2,3,6-tetrahydropyridin-4-yl)-1H-indole (1.6 g), 19a (2.0 g), $K_2CO_3$ (4.0 g), and methylisobutylketone (20 ml) was refluxed for 16 hours. The mixture was filtered and evaporated in vacuo, and the residue was purified on silica gel eluted with ethyl acetate-methanol-triethylamine (90:5:5). Crystallization from ethanol gave the title product (0.3 g).

Mp 172–4° C. $^1$H NMR (DMSO-$d_6$) d 1.75–1.95 (m, 1H). 2.05–2.20 (m, 1H), 2.25 (s, 3H), 2.50–2.65 (m, 4H), 2.75 (t, 2H), 3.25 (broad s, 2H), 3.45–3.60 (m, 1H), 3.80 (dd, 2H), 4.20 (t, 1H), 6.15 (broad s, 1H), 7.00–7.15 (m, 3H), 7.25 (d, 1H), 7.45 (d, 2H), 7.80 (d, 1H), 8.15 (s, 1H) 8.25 (d, 1H). MS m/z (%): 420 (MH+, 7%), 174 (100%), 144 (55%).

In a similar manner the following compounds were prepared:

3-[1-[2-(1-Acetyl-2,3-dihydro-1H-indol-3-yl)ethyl] piperidin-4-yl]-6-chloro-1H-indole, 20b.

From 19a and 6-chloro-3-(piperidin-4-yl)-1H-indole (EP Patent publication No 465398-A1). Mp 188–90° C. $^1$H NMR (DMSO-$d_6$) d 1.70–1.90 (m, 3H), 1.95–2.20 (m, 5H), 2.25 (s, 3H), 2.40–2.55 (m, 2H), 2.80 (tt, 1H), 3.00–3.10 (m, 2H), 3.40–3.55 (m, 1H), 3.75 (dd, 1H), 4.20 (t, 1H), 6.95 (d, 1H), 7.05 (ddd, 1H), 7.25 (dt, 1H), 7.35 (d, 1H), 7.55 (d, 1H), 8.00 (s, 1H), 8.25 (d, 1H). MS m/z (%): 422 (MH+, 100%), 249 (15%), 146 (19%).

6-Chloro-3-[1-[2-(1-formyl-2,3-dihydro-1H-indol-3-yl) ethyl]-1,2,3,6-tetrahydropyridin-4yl]-1H-indole. 20c.

From 19b and 6-chloro-3-(1,2,3,6-tetrahydropyridin-4-yl)-4H-indole.

Mp 183–5° C. (from acetone). $^1$H NMR (DMSO-$d_6$, the spectrum shows hindered rotation which is eliminated by heating above 100° C.) δ1.60–1.80 (m, 1H), 1.95–2.10 (m, 1H), 2.35–2.55 (m, 4H), 2.70 (t, 2H), 3.15 (s, 2H), 3.35–3.55 (m, 1H), 3.65 (dd, 0.76H), 3.90 (dd, 0.24H), 4.10 (t, 0.76H), 4.30 (t, 0.24H), 6.15 (s, 1H), 6.95–7.15 (m, 2H), 7.25 (t, 1H), 7.35 (d, 1H), 7.40–7.50 (m, 3H), 7.80 (d, 0.76H), 7.90 (d, 0.24H), 8.50 (s, 0.24H), 9.05 (s, 0.76H), 11.20 (s, 1H). MS m/z (%): 406 (MH+, 100%), 3.77 (5%), 244 (15%).

6-Chloro-3-[1-[2-(1-formyl-2,3-dihydro-1H-indol-3-yl) ethyl]piperidin-4-yl]-1H-indole, oxalate, 20d.

From 19b and 6-chloro-3-(piperidin-4-yl)-1H-indole. Mp 143–145° C. $^1$H NMR (DMSO-$d_6$ the spectrum shows hindered) δ1.75–2.30 (m, 6H), 2.65–3.10 (m, 5H), 3.30–3.55 (m, 3H), 3.65 (dd, 0.8H), 3.90 (dd, 0.2H), 4.10 (t, 0.8H), 4.25 (t, 0.2H), 6.95 (dd, 1H), 7.00–7.40 (m, 5H), 7.45 (d, 0.8H), 7.60 (d, 1H), 7.95 (d, 0.2H), 8.50 (s, 0.2H), 9.05 (s, 0.8H), 11.10 (s, 1H). MS m/z (%): 410, 408 (MH+, 9%, 25%), 146 (11%), 98 (100%).

3-[1-[2-(1-Acetyl-5-bromo-2,3-dihydro-1H-indol-3-yl) ethyl]-1,2,3,6-tetrahydropyridin-4yl]-6-chloro-1H-indole, oxalate 20e.

From 19 c and 6-chloro-(1.2,3,6-tetrahydropyridin-4-yl)-1H-indole. Mp 157–159° C. $^1$H NMR (DMSO-$d_6$) δ1.80–2.00 (m, 1H), 2.10–2.40 (m, 1H), 2.20 (s, 3H), 2.70 (broad s, 2H), 2.90–3.15 (m,. 2H), 3.20 (broad s, 2H), 3.45–3.60 (m, 1H), 3.65 (broad s, 2H), 3.85 (dd, 1H), 4.25 (t, 1H), 6.15 (broad s, 1H), 7.10 (dd, 1H), 7.35 (dd, 1H), 7.45 (d, 1H), 7.55 (s, 2H), 7.85 (d, 1H), 8.00 (d, 1H), 11.45 (broad s, 1H). MS m/z (%): 502, 500, 498 (MH+, 8%, 27%, 22%), 297 (95%), 295 (100%).

3-[1-[2-(1-Acetyl-2,3-dihydro-1H-indol-3-yl)ethyl]-1,2,3,6-tetrahydropyridin-4-yl]-7-chloro-1H-indole, oxalate 20f.

From 19a and 7-chloro-(1,2,3,6-tetrahydropyridin-4-yl)-1H-indole.Mp 171–173° C. $^1$H NMR (DMSO-$d_6$) δ1.90–2.00 (m, 1H), 2.20 (s, 3H), 2.20–2.30 (m, 1H), 2.80 (broad s, 2H), 3.10–3.30 (m, 2H), 3.40 (broad s, 2H), 3.50 (t, 1H), 3.80–3.95 (m, 3H), 4.25 (t, 1H), 6.15 (broad s, 1H), 6.95–7.15 (m, 2H), 7.15–7.25 (m, 2H), 7.35 (d, 1H), 7.60 (s, 1H), 7.80 (d, 1H), 8.05 (d, 1H), 11.65 (broad s, 1H). MS m/z (%): 422, 420 (MH+, 3%, 7%), 174 (100%), 144 (43%).

3-[1-[2-(1-Acetyl-2,3-dihydro-1H-indol-3-yl)ethyl]-1,2,3,6-tetrahydropyridin-4-yl]-6,7-dichloro-1H-indole, oxalate 20g.

From 19a and 6,7-dichloro-(1,2,3,6-tetrahydropyridin-4-yl)-1H-indole. Mp 115–117° C. $^1$H NMR (DMSO-$d_6$) δ1.90–2.05 (m, 1H), 2.20 (s, 3H), 2.20–2.35 (m, 1H), 2.80 (broad s, 2H), 3.10–3.30 (m, 2H), 3.40 (broad s, 2H), 3.50 (broad s, 1H), 3.80–3.95 (m, 3H), 4.25 (t, 1H), 6.15 (broad s, 1H), 7.05 (t, 1H), 7.20 (t, 1H), 7.25 (d, 1H), 7.35 (d, 1H), 7.65 (s, 1H), 7.80 (d, 1H), 8.05 (d, 1H), 11.90 (broad s, 1H). MS m/z (%): 456, 454 (MH+, 4%, 6%), 217 (36%), 174 (100%), 144 (36%).

3-[1-[2-(1-Acetyl-2,3-dihydro-1H-indol-3-yl)ethyl]-1,2,3,6-tetrahydropyridin-4-yl]-5,6-methylenedioxy-1H-indole, oxalate 20h.

From 19a and 5,6-methylenedioxy-(1,2,3,6-tetrahydropyridin-4-yl)-1H-indole.Mp 182–183° C. $^1$H NMR (DMSO-$d_6$) δ1.90–2.00 (m, 1H), 2.20 (s, 3H), 2.20–2.30 (m, 1H), 2.75 (broad s, 2H), 3.10–3.30 (m, 2H), 3.40 (broad s, 2H), 3.50 (broad s, 1H), 3.80–3.90 (m, 3H), 4.20 (t, 1H), 5.95 (s, 2H), 6.05 (broad s, 1H), 6.95 (s, 1H), 7.05 (t, 1H), 7.20 (t, 1H), 7.25–7.40 (m, 3H), 8.05 (d, 1H), 11.15 (broad s, 1H). MS m/z (%): 430 (MH+, 6%), 217 (26%), 174 (100%), 144 (62%).

3-[1-[2-(1-tert-Butoxycarbonyl-2,3-dihydro-1H-indol-3-yl) ethyl]-1,2,3,6-tetrahydropyridin-4-yl]-6-chloro-1H-indole, oxalate 20i.

From 19 d and 6-chloro-(1,2,3,6-tetrahydropyridin-4-yl)-1H-indole. Mp 132–135° C. $^1$H NMR (DMSO-$d_6$) δ1.55 (s, 9H), 1.90–2.00 (m, 1H), 2.20–2.30 (m, 1H), 2.80 (broad s, 2H), 3.10–3.25 (m, 2H), 3.40 (broad s, 3H), 3.65 (dd, 1H), 3.85 (broad s, 2H), 410 (t, 1H), 6.15 (broad s, 1H), 6.95 (t, 1H), 7.10 (d, 1H), 7.20 (t, 1H), 7.30 (d, 1H), 7.50 (s, 1H), 7.55 (s, 1H), 7.60–7.80 (broad s, 1H), 7.85 (d, 1H), 11.60 (broad s, 1H). MS m/z (%): 478 (MH+, 10%), 219 (100%), 144 (27%).

5-[4-[2-(1-Acetyl-2,3-dihydro-1H-indol-3-yl)ethyl] piperazin-1-yl]-1H-indole, hydrochloride. 20j.

Prepared from 19a and 5-piperazinyl-1H-indole. Mp 241–243° C. $^1$H NMR (DMSO-$d_6$) δ1.95–2.15 (m, 1H), 2.20 (s, 3H), 2.25–2.35 (m, 1H), 3.15–3.50 (m, 6H), 3.55 (broad s, 1H), 3.70 (d, 4H), 3.90 (dd, 1H), 4.25 (t, 1H), 6.40 (s, 1H), 6.95–7.10 (m, 2H), 7.20 (t, 1H), 7.25–7.45 (m, 4H), 8.05 (d, 1H), 11.10 (s, 1H). MS m/z (%): 389 (MH+, 71%), 159 (71%), 118 (100%).

3-[1-[3-(1-Acetyl-2,3-dihydro-1H-indol-3-yl)propyl]-1,2,3,6-tetrahydropyridin-4-yl]-6-chloro-1H-indole, oxalate 20k. From compound 22a.

Mp 112–115° C. $^1$H NMR (DMSO-$d_6$) δ1.45–1.60 (m, 1H), 1.70–1.90 (m, 3H), 2.20 (s, 3H), 2.80 (broad s, 2H), 3.15 (broad s, 2H), 3.30–3.50 (m, 3H), 3.70–3.90 (m, 3H), 4.25 (t, 1H), 6.15 (broad s, 1H), 7.00 (t, 1H), 7.10 (d, 1H), 7.20 (t, 1H), 7.30 (d, 1H), 7.45 (s, 1H), 7.55 (s, 1H), 7.85 (d, 1H), 8.05 (d, 1H), 11.60 (broad s, 1H). MS m/z (%): 436, 434 (MH+, 2%, 5%), 231 (100%), 189 (36%), 158 (70%).

3-[1-[2-(1-Acetyl-5-fluoro-2,3-dihydro-1H-indol-3-yl) ethyl]-1,2,3,6-tetrahydropyridin-4-yl]-6-chloro-1H-indole, 20l.

Prepared from 19f and 6-chloro-(1,2,3,6-tetrahydropyridin-4-yl)-1H-indole. Mp 183–185° C. $^1$H NMR (DMSO-$d_6$) d 1.65–1.75 (m, 1H), 2.00–2.10 (m, 1H), 2.15 (s, 3H), 2.40–2.55 (m, 4H), 2.60–2.75 (m, 2H), 3.05–3.25 (dd, 2H), 3.45 (bs, 1H), 3.80–3.90 (m, 1H), 4.25 (t, 1H), 6.10 (bs, 1H), 6.95 (t, 1H), 7.05 (d, 1H), 7.15 (d, 1H), 7.40 (s, 2H), 7.80 (d, 1H), 8.05 (m, 1H), 11.20 (bs, 1H). MS m/z (%): 438 (MH+, 7%), 162 (100%), 192 (63%), 235 (58%).

3-[1-[2-(1-Acetyl-5-methyl-2,3-dihydro-1H-indol-3-yl) ethyl]-1,2,3,6-tetrahydropyridin-4-yl]-6-chloro-1H-indole, 20m.

Prepared form 19g and 6-chloro-(1,2,3,6-tetrahydropyridin-4-yl)-1H-indole. Mp 179–181° C. $^1$H NMR (DMSO-$d_6$) d 1.60–1.70 (m, 1H), 1.95–2.05 (m, 1H), 2.15 (s, 3H), 2.25 (s, 3H), 2.40–2.60 (m, 4H), 2.65 (bs, 2H), 3.05–3.20 (dd, 2H), 3.40 (bs, 1H), 3.75–3.85 (m, 1H), 4.20 (t, 1H), 6.10 (bs, 1H), 6.90 (d, 1H), 7.00 (d, 1H), 7.05 (s, 1H), 7.40 (s, 2H), 7.80 (d, 1H), 7.90 (d, 1H), 11.25 (bs, 1H). MS m/z(%): 434 (MH+, 3%), 188 (100%), 158 (31%), 231 (21%).

EXAMPLE 21

6-Chloro-3-[1-(indan-2-ylmethyl)piperidin-4yl]-1H-indole oxalate, 21a

To a solution of 11a (0.51 g) in ethanol (40 ml) and acetic acid (10 ml) was added platinum oxide (0.12 g). The mixture was shaken for 4.5 hours under 3 atm. hydrogen pressure. The mixture was filtered and evaporated in vacuo. The residue was dissolved in $CH_2Cl_2$ and the organic phase was shaken with dilute ammoniumhydroxide and then worked up in a conventional manner to give 0.46 g of crude product, from which the title product was crystallized as the oxalate salt from acetone. Yield 0.36 g, mp 229–30° C. $^1$H NMR (DMSO-$d_6$) d 1.85–2.10 (m, 4H), 2.65–3.15 (m, 10H), 3.50 (d, 2H), 7.00 (dd, 1H), 7.10–7.20 (m, 2H), 7.20–7.30 (m, 3H), 7.40 (d, 1H), 7.65 (d, 1H), 11.05 (s, 1H). MS m/z (%): 365 (MH+, 100%), 249 (17%), 131 (20%).

In a similar manner the following compounds were prepared:

3-[1-(indan-2-ylmethyl)piperidin-4-yl]-1H-indole 21b.

Prepared from 11b. Mp 146–147° C. $^1$H NMR ($CDCl_3$) δ1.85 (q, 2H), 2.05 (d, 2H), 2.20 (t, 2H), 2.45 (d, 2H), 2.65–2.90 (m, 4H), 3.00–3.20 (m, 4H), 6.95 (s, 1H), 7.05–7.30 (m, 6H), 7.35 (d, 1H), 7.65 (d, 1H), 7.95 (broad s, 1H). MS m/z (%): 331 (MH+, 11%), 131 (11%), 98 (100%).

7-Chloro-3-[1-(indan-2-ylmethyl)piperidin-4-yl]-1H-indole, oxalate 21c.

Prepared from 11c. Mp 218–219° C. $^1$H NMR (DMSO-d$_6$) δ2.00–2.25 (m, 4H), 2.70–2.85 (m, 2H), 2.85–3.35 (m, 8H), 3.35 (d, 2H), 7.00 (t, 1H), 7.10–7.30 (m, 6H), 7.65 (d, 1H), 11.30 (broad s, 1H). MS m/z (%): 367, 365 (MH+, 9%, 25%), 131 (14%), 98 (100%).

6,7-Dichloro-3-[1-(indan-2-ylmethyl)piperidin-4-yl]-1H-indole, 21d.

Prepared from 11d. Mp 141–142° C. $^1$H NMR (CDCl$_3$) δ1.75–1.90 (m, 2H), 2.00 (d, 2H), 2.15 (t, 2H), 2.45 (d, 2H), 2.65–2.85 (m, 4H), 3.00–3.15 (m, 4H), 7.00 (s, 1H), 7.10–7.25 (m, 5H), 7.45 (d, 1H), 8.20 (broad s, 1H). MS m/z (%): 401, 399 (MH+, 17%, 26%), 131 (19%), 98 (100%).

3-[1-(Indan-2-ylmethyl)piperidin-4-yl]-5,6-methylenedioxy-1H-indole, 21e.

Prepared from 11e. Mp 187–188° C. $^1$H NMR (DMSO-d$_6$) δ1.55–1.70 (m, 2H), 1.90 (d, 2H), 2.05 (t, 2H), 2.30 (d, 2H), 2.60–2.75 (m, 4H), 2.85–3.05 (m, 4H), 5.90 (s, 2H), 6.85 (s, 1H), 6.90 (s, 1H), 7.00 (s, 1H), 7.05–7.15 (m, 2H), 7.15–7.25 (m, 2H), 10.55 (broad s, 1H). MS m/z (%): 375 (MH+, 10%), 131 (9%). 98 (100%).

6-Chloro-3-[1-[2-(indan-2-yl)ethyl]piperidin-4-yl]-1H-indole, 21f.

Prepared from 11g. Mp 155–156° C. $^1$H NMR (DMSO-d$_6$) δ1.60–1.75 (m, 4H), 1.90 (d, 2H), 2.05 (t, 2H), 2.35–2.45 (m, 3H), 2.45–2.60 (m, 2H), 2.70 (t, 1H), 2.90–3.05 (m, 4H), 6.95 (d, 1H), 7.05–7.20 (m, 5H, 7.35 (s, 1H), 7.55 (d, 1H), 10.90 (broad s, 1H). MS m/z (%): 381, 379 (MH+, 33%, 89%), 228 (45%), 145 (44%), 98 (100%).

6Chloro-3-[1-[3-(indan-2-yl)propan-1-yl]piperidin-4-yl]-1H-indole, 21g

Prepared from 11 h. Mp 134–135° C. $^1$H NMR (CDCl$_3$) δ1.45–1.60 (m, 2H), 1.60–1.75 (m, 2H), 1.75–1.90 (m, 2H), 2.05 (d. 2H), 2.10 (t, 2H), 2.35–2.55 (m, 3H), 2.55–2.65 (m, 2H), 2.80 (t, 1H), 2.95–3.15 (m, 4H), 6.95 (s, 1H), 7.00–7.25 (m, 5H), 7.30 (s, 1H), 7.55 (d, 1H), 8.10 (broad s, 1H). MS m/z (%): 395, 393 (MH+, 8%, 21%), 242 (53%), 117 (52%), 98 (100%).

6-Chloro-3-[1-[4-(indan-2-yl)butan-1-yl]piperidin-4-yl]-1H-indole, 21h.

Prepared from 11i. Mp 139–140° C. $^1$H NMR (CDCl$_3$) δ1.30–1.70 (m, 6H), 1.70–1.95 (m. 2H), 1.95–2.20 (m, 4H), 2.35–2.65 (m, 5H), 2.70–2.90 (m, 1H), 2.95–3.15 (m, 4H), 6.95 (d, 1H:), 7.00–7.25 (m, 5H), 7.35 (d, 1H), 7.55 (d, 1H), 8.05 (broad s, 1H). MS m/z (%): 409, 407 (MH+, 32%,(, 90%), 256 (96%), 98 (100%).

EXAMPLE 22

1-Acetyl-3-(3-bromopropan-1-yl)-2,3-dihydro-]-1H-indole, 22a (Intermediate)

A mixture of 3-(1H-indol-3-yl)propionic acid (10 g), methanol (200 ml), and a saturated solution of HCl in ether (75 ml) was stirred at room temperature for 4 days. The solvents were removed in vacuo, and the residue was worked up in a conventional manner by the use of dilute ammonium hydroxide and ethyl acetate to yield an oil (10.6 g). The oil was dissolved in acetic acid (200 ml), and NaCNBH$_4$ (12 g) was added in parts of 1 g. The mixture was stirred at room temperature for 48 h, and then poured into ice-cooled water. The pH of the solution was adjusted to 8 with ammonium hydroxide (25%), and the aqueous phase was extracted with ether. The combined organic phases were extracted with 1 M HCl solution. The pH of the aqueous phase was adjusted to 8 with ammonium hydroxide and extracted with ethyl acetate. The combined organic extracts were washed with brine, dried (MgSO$_4$), and the solvent was removed in vacuo. The residue was purified on silica gel eluted with ethyl acetate-heptane (1:1) to give an oil (6.1 g). The residue was dissolved in THF (50 ml) and added to a suspension of LiAlH$_4$ (2.0 g) in THF (100 ml) at about 30° C. The mixture was stirred at room temperature for 15 min and then cooled to 5° C. By drop-wise addition, water (4.0 ml), 15% NaOH solution (2.0 ml), and water (10 ml) was added. The mixture was dried (MgSO$_4$) and concentrated in vacuo. The oil was dissolved in THF (200 ml), added triethylamine (11 ml) and cooled to −20° C. To this mixture, a solution of acetyl chloride (2.1 ml) in THF (50 ml) was added, and the mixture was allowed to warm to 5° C. To this mixture, a solution of methanesulfonyl chloride (2.1 ml) in THF (50 ml) was added. Ether (200 ml) was added and the mixture was filtered. The mother liquid was concentrated in vacuo and subjected to purification on silica gel eluted with ethyl acetate-heptane (4:1) to give a crystalline compound (7.3 g). The compound was dissolved in acetone (500 ml), added lithium bromide (10.3 g), and the mixture was boiled under reflux for 1 h. The mixture was cooled, filtered and evaporated in vacuo to dryness to give the title compound.

The following compound was made in a similar manner:

1-Acetyl-2,3-dihydro-3-(2-iodoethyl)-1H-indole, 22b. From 19a and lithium iodide.

2-Iodomethylindane, 22c. From 2-indanemethanol methanesulfonate prepared from 9a as described in Example and 3.

EXAMPLE 23

7-Methoxy-1-indanecarboxylic acid, 23a (Intermediate)

A mixture of 7-methoxy-1-indanone (25 g), prepared according to J. Am. Chem. Soc. 1948, 70, 1386, ZnI$_2$ (0.5 g) in toluene (300 ml) was added trimethylsilyl cyanide (25 ml and further 15 ml after 3 h), and the reaction mixture was stirred at 60° C. for 5 h. Water was added, and the mixture stirred at room temperature for 1 h. The phases were separated, and the organic phase was dried (MgSO$_4$) and evaporated to dryness in vacuo. The residue was purified on silica gel eluted with dichloromethane (25 g). The residue was dissolved in acetic acid (100 ml) and 6 M HCl solution (100 ml), and the mixture was heated at 100° C. for 7 h. Acetic acid was removed in vacuo, and the aqueous phase was extracted with ether. The combined organic phases were dried (MgSO$_4$), evaporated to dryness in vacuo and purified on silica gel eluted with dichloromethane (5 g). The residue was dissolved in ethanol (200 ml), the solution was added palladium on carbon (5%) (2 g), and the mixture was shaken for 3 h under 3 atm. hydrogen pressure. The mixture was filtered and evaporated in vacuo (5 g). The residue was dissolved in acetic acid (10 ml), concentrated sulfuric acid (5 ml), and water (5 ml), and the mixture was heated at 110° C. for 3 h. The mixture was cooled and extracted with ethyl acetate. The organic phases were washed with water, added ether and extracted with 2 M NaOH solution. The pH of the aqueous phase was adjusted to 1 with hydrochloric acid and extracted with ether. The combined organic phase was dried (MgSO$_4$) and evaporated to dryness in vacuo to give the title compound (2 g).

The following compound was made in a similar manner:

6-Methoxy-1-indanecarboxylic acid, 23b. From 6-methoxy-1-indanone.

EXAMPLE 24

2-(2-Iodoethyl)indane, 24a (Intermediate)

A mixture of 2-(indan-2-yl)ethanol (19.3 g), imidazole (12.1 g), triphenylphosphine (34.3 g), and toluene (250 ml)

was heated to 90° C. To this mixture, iodide (33.2 g) was added, and the resulting mixture was stirred at 90° C. for 20 min. The mixture was allowed to cool to room temperature. filtered, and concentrated in vacuo. The residue was purified on silica gel eluted with ethyl acetate-heptane (1:4) to give an oil (28.4 g, 87%).

EXAMPLE 25

4-[4-[2-(Indan-2-yl)ethyl]piperazin-1-yl]-1H-indole, 25a

A mixture of 4-(piperazin-1-yl)-1H-indole (1.5 g), 2-(2-iodoethyl)indane (2.0 g), $K_2CO_3$, methyl isobutyl ketone (150 ml), and N-methylpyrrolidone (10 ml) was boiled under reflux for 3 h. The mixture was allowed to cool to room temperature, filtered, and concentrated in vacuo. The residue was purified on silica gel eluted with ethyl acetate-heptane (1:2) to give a crystalline compound, which was recrystallized (ethyl acetate) to give the title compound (1.2 g, 47%).

Mp146–147° C. $^1$H NMR (CDCl$_3$) δ1.70–1.85 (m, 2H), 2.40–2.70 (m, 5H), 2.75 (broad s, 4H), 3.00–3.15 (m, 2H), 3.30 (broad s, 4H), 6.55 (s, 1H), 6.60 (d, 1H), 7.00–7.30 (m, 7H), 8.20 (broad s, 1H). MS m/z (%): 346 (MH+, 34%), 159 (88%), 145 (100%).

The following compound was made in a similar manner:
5-[4-[2-(Indan-2-yl)ethyl]piperazin-1-yl]-1H-indole, hydrochloride 25b. Prepared 2.40–2.55 from 24a and 5-(piperazin-1-yl)-1H-indole. Mp 251–253° C. $^1$H NMR (DMSO-d$_6$) δ1.90–2.05 (m, 2H),(m, 1H), 2.55–2.70 (m, 2H), 3.00–3.15 (m, 2H), 3.25 (broad s, 2H), 3.50 (broad s, 1H), 3.75 (broad s, 6H), 6.45 (s, 1H), 7.05–7.30 (m, 5H), 7.40 (s, 1H), 7.45 (d, 1H), 7.55 (broad s, 1H), 11.30 (broad s, 1H). MS m/z (%): 346 (MH+, 44%), 159 (87%), 145 (100%).

EXAMPLE 26

5-Chloro-1-(pyridin-4-yl)-1H-indole , 26a
(Intermediate)

A mixture of 5-chloro-1H-indole (20 g), 4-bromopyridine, HCl (45 g), $K_2CO_3$ (55 g), CuBr (5 g), and Cu (2 g) was heated at 150° C. for 24 h. The reaction mixture was cooled, poured into water (700 ml), and crude product was collected by filtration. The crude product was dissolved in ethyl acetate (1000 ml), and the organic phase was washed with dilute ammonium hydroxide and saturated NaCl solution. The organic phase was dried (MgSO4), and concentrated in vacuo (150 ml). Crystalline 5-chloro-1-(pyridin-4-yl)-1H-indole was collected by filtration (18.0 g. 60%).
The following compound was made in a similar manner:
1-(Pyridin-4-yl)-1H-indole, 26b.

EXAMPLE 27

2-(Pyridin-4-yl)-1H-indole, 27a
(Intermediate)

A mixture of isonicotic acid (7.1 g) and thionyl chloride (150 ml) was boiled under reflux for 2 h and evaporated to dryness in vacuo. The residue was dissolved in DMF (100 ml) and added to a suspension of 2-aminobenzyltriphenylphosphonium bromide (L. Capuano et al, Chem. Ber. 1986. 119, 2069–2074) in dichloromethane. The resulting clear solution was stirred at room temperature for 2 h and concentrated in vacuo. The rude product was recrystallized (ethanol) to give 21.3 g of crystals. Compound corresponding to 1.0 g was suspended in toluene (25 ml), and the mixture was heated to reflux temperature. Potassium tert-butoxide (0.44 g) was added at once, and the reaction mixture was boiled under reflux for 15 min, filtered hot, and concentrated in vacuo. Purification on silica gel eluted with ethyl acetate-heptane-TEA (80:20:5) gave the title compound.

EXAMPLE 28

5-Chloro-1-[1-[2-(indan-2-yl)ethyl]-1,2,3,6-tetrahydropyridin-4-yl]-1H-indole 28a A mixture of 5-chloro-1-(pyridin-4-yl)-1H-indole 26a (4.0 g), 2-(2-iodoethyl)indane 24a (4.8), and methyl isobutyl ketone (100 ml) was boiled under reflux for 20 h. The mixture was cooled, and a crystalline compound collected by filtration (6.5 g). Compound corresponding to 5.5 g was suspended in methanol (100 ml), and NaBH$_4$ (1.5 g) was added in parts of 0.5 g. The resulting mixture was stirred at room temperature for 1 h, and the solvent was removed in vacuo. Conventional work up with ethyl acetate and water followed by purification on silica gel eluted with ethyl acetate-heptane (1:1) gave the crude product, which was crystallized (ethyl acetate) to give the title compound (1.1 g, 27%).

Mp 93–94° C. $^1$H NMR (CDCl$_3$) δ1.75–1.90 (m, 2H). 2.45–2.55 (m, 1H), 2.55–2.70 (m, 6H), 2.75–2.90 (m, 2H), 3.05–3.15 (m, 2H), 3.25 (d, 2H), 5.90 (broad s, 1H), 6.45 (s, 1H), 7.05–7.25 (m, 6H), 7.45 (d, 1H), 7.60 (s, 1H). MS m/z (%): 377 (MH+, 6%), 143 (100%), 128 (50%).

The following compound was made in a similar manner:
1-[1-[2-(Indan-2-yl)ethyl]-1,2,3,6-tetrahydropyridin-4-yl]-1H-indole, oxalate 28b.
Prepared from 24a and 26b.Mp 176–178° C. $^1$H NMR (DMSO-d$_6$) δ1.85–1.95 (m, 2H), 2.40–2.55 (m, 1H), 2.55–2.70 (m, 2H), 2.85 (broad s, 2H), 3.00–3.10 (m, 2H), 3.15 (t, 2H), 3.40 (broad s, 2H), 3.85 (broad s, 2H), 5.95 (broad s, 1H), 6.60 (d, 1H), 7.05–7.25 (m, 6H), 7.55 (d, 1H), 7.60–7.70 (m, 2H. MS m/z (%): 343 (MH+), 143 (100%), 128 (80%).
2-[1-[2-(Indan-2-yl)ethyl]-1,2,3,6-tetrahydropyridin-4-yl]-1H-indole, 28c.
Prepared from 27a and 24a. Mp 175–176    C. $^1$H NMR (CDCl$_3$) δ1.75–1.85 (m, 2H), 2.45–2.55 (m, 1H), 2.55–2.60 (m, 2H), 2.60–2.70 (m, 4H), 2.70–2.80 (m, 2H), 3.05–3.15 (m, 2H), 3.25 (broad s, 2H), 6.05 (broad s, 1H), 6.45 (s, 1H), 7.05 (t, 1H), 7.10–7.25 (m, 5H), 7.35 (d, 1H), 7.55 (d, 1H), 8.10 (broad s, 1H). MS m/z (%): 343 (MH+, 8%), 174 (32%), 143 (100%).
2-[1-(Indan-2-yl)methyl-1,2,3,6-tetrahydropyridin-4-yl]-1H-indole, 28d.
From 22c and 27a. $^1$H NMR (CDCl$_3$) d 2.50–2.55 (m, 2H), 2.65 (broad s, 2H), 2.70–2.85 (m, 5H), 3.00–3.15 (m, 2H), 3.25 (d, 2H), 6.05 (broad s, 1H), 6.45 (s, 1H), 7.05 (t, 1H), 7.10–7.25 (m, 5H), 7.30 (d, 1H), 7.55 (d, 1H), 8.10 (broad s, 1H). MS m/z (%): 329 (MH+, 5%), 160 (4%), 131 (4%), 91 (6%), 44 (100%).
2-[1-[2-(1-Acetyl-2,3-dihydro-1H-indol-3-yl)ethyl]-1,2,3,6-tetrahydropyridin-4-yl]-1H-indole 28e.
From 22b and 27a. $^1$H NMR (DMSO-d$_6$) d 1.65–1.80 (m, 1H), 1.95–2.10 (m, 1H), 2.15 (s, 3H), 2.45–2.60 (m, 4H), 2.65 (broad s, 2H), 3.10–3.20 (m, 2H), 3.40–3.50 (m, 1H), 3.75–3.85 (m, 1H), 4.20 (t, 1H), 6.30 (s, 1H), 6.40 (s, 1H), 6.90 (t, 1H), 6.95–7.10 (m, 2H), 7.15 (t, 1H), 7.25–7.35 (m, 2H), 7.45 (d, 1H), 8.05 (d, 1H), 11.05 (broad s, 1H). MS m/z (%): 386 (MH+, 13%), 217 (20%), 174 (10%), 144 (87%), 132 (45%), 44 (100%).

EXAMPLE 29

5-Chloro-1-[1-[2-(indan-2-yl)ethyl]piperidin-4-yl]-1H-indole, 29a

A mixture of 5-Chloro-1-[1-[2-(indan-2-yl)ethyl]-1,2,3,6-tetrahydropyridin-4yl]-1H-indol. 28a. (1.9 g), acetic acid (50 ml), and platinum oxide (0.1 g) was shaken for 3 h under 3 atm. hydrogen pressure. The mixture was filtered and evaporated in vacuo. The residue was dissolved in ethyl acetate and the organic phase was shaken with dilute ammonium hydroxide and then worked up in a conventional manner. Further purification was done on silica gel eluted with ethyl acetate-heptane (1:1) to give 2.0 g of crude product. The crude product was crystallized (ethyl acetate), and the title compound was collected by filtration (1.1 g, 58%).

Mp 108–109° C. $^1$H NMR (CDCl$_3$) δ1.70–1.80 (m, 2H), 2.00–2.10 (m, 4H), 2.10–2.25 (m, 2H), 2.40–2.55 (m, 3H), 2.55–2.70 (m, 2H), 3.00–3.20 (m, 4H), 4.10–4.25 (m, 1H), 6.45 (d, 1H), 7.05–7.35 (m, 7H), 7.60 (s, 1H). MS m/z (%): 379 (MH+, 3%), 228 (13%), 145 (29%), 143 (28%), 98 (100%).

The following compound was made in a similar manner:

1-[1-[2-(Indan-2-yl)ethyl]piperidin-4-yl]-1H-indole, 29b. Prepared from 28b. Mp 80–81° C. $^1$H NMR (CDCl$_3$) δ1.70–1.85 (m, 2H), 2.00–2.25 (m, 6H), 2.40–2.55 (m, 3H), 2.55–2.70 (m, 2H), 3.00–3.20 (m, 4H), 4.15–4.30 (m, 1H), 6.50 (d, 1H), 7.05–7.30 (m, 7H), 7.40 (d, 1H), 7.65 (d, 1H). MS m/z (%): 345 (MH+, 4%), 228 (9%), 145 (30%), 143 (34%), 98 (100%).

EXAMPLE 30

6-Chloro-3-[1-[2-(2,3-dihydro-1H-indol-3-yl)ethyl]-1,2,3,6-tetrahydropyridin-4-yl]-1H-indole, oxalate 30a A mixture of 3-[1-[2-(1-tert-butoxycarbonyl-2,3-dihydro-1H-indol-3-yl)ethyl]-1,2,3,6-tetrahydro-pyridin-4-yl]-6-chloro-1H-indole, oxalate 20i as the free base (4.0 g), dichloromethane (50 ml), and THF (25 ml) was cooled in an ice bath, and the mixture was added trifluoroacetic acid (40 ml). The reaction mixture was stirred at room temperature for 16 h and poured into an ice-cold solution of dilute ammonium hydroxide. Conventional work up with ethyl acetate gave the crude product. Crude product corresponding to 1.4 g was converted to the oxalate salt, which was recrystallized (methanol-ether-heptane) to give the title compound (0.5 g).

Mp 109–111° C. $^1$H NMR (DMSO-d$_6$) δ1.80–2.00 (m, 1H), 2.10–2.30 (m, 1H), 2.80 (broad s, 2H), 3.05–3.35 (m, 4H), 3.35–3.65 (m, 3H), 3.90 (broad s, 2H), 6.15 (broad s, 1H), 6.45–6.65 (m, 2H), 6.95 (t, 1H), 7.00–7.15 (m, 2H), 7.45 (d, 1H), 7.60 (d, 1H), 7.85 (d, 1H), 11.55 (d, 1H). MS m/z (%): 378 (MH+, 4%), 169 (19%), 168 (38%), 144 (100%).

The following compound was made in a similar manner:

6-Chloro-3-[1-[4-(2,3-dihydro-1H-indol-3-yl)butan-1-yl]-1,2,3,6-tetrahydropyridin-4yl]-1H-indole 30b. From 19e.

EXAMPLE 31

6-Chloro-3-[1-[2-(2,3-dihydro-1-methylaminocarbonyl-1H-indol-3-yl)ethyl]-1,2,3,6-tetrahydropyridin-4-yl]-1H-indole oxalate, 31a To a solution of 6-chloro-3-[1-[2-(2,3-dihydro-1H-indol-3-yl)ethyl]-1,2,3,6-tetrahydropyridin-4-yl]-1H-indole, oxalate 30a, as the free base, (3.6 g) in dichloromethane (100 ml) was added methylisocyanate (1.4 g) in dichloromethane (20 ml). The mixture was stirred at room temperature for 16 h, and the solvent was removed in vacuo. The residue was purified on silica gel eluted with ethyl acetate-ethanol-triethylamine (90:10:5) to give the crude product, which was recrystallized (methanol-ethyl acetate-ether) to give the title compound (1.8 g). $^1$H NMR (DMSO-d$_6$) δ1.60–1.70 (m, 1H), 1.95–2.05 (m, 1H), 2.40–2.60 (m, 4H), 2.60–2.75 (m, 5H), 3.15 (q, 2H), 3.35–3.50 (m, 1H), 3.55–3.65 (m, 1H), 4.00 (t, 1H), 6.10 (broad s, 1H), 6.55 (d, 1H), 6.85 (t, 1H), 7.05 (d, 1H), 7.10 (t, 1H), 7.20 (d, 1H), 7.45 (s, 2H), 7.80 (d, 1H), 7.85 (d, 1H), 11.25 (broad s, 1H). MS m/z (%): 437, 435 (MH+, 2%, 6%), 201 (54%), 189 (100%), 144 (64%).

EXAMPLE 32

(+/−)-Methyl (1-tert-Butoxycarbonyl-2,3-dihydro-1H-indol-3-yl)acetate 32a (Intermediate)

A mixture of (1H-indol-3-yl)acetic acid (62 g), methanol (800 ml), and a saturated solution of HCl in ether (200 ml) was stirred at room temperature for 4 days. The solvents were removed in vacuo, and the residue worked up in a conventional manner by the use of dilute ammonium hydroxide and ethyl acetate to yield an oil (64 g). The oil was dissolved in acetic acid (600 ml), and NaCNBH$_4$ (27.6 g) was added in parts of 1 g. The mixture was stirred at room temperature for 48 h, and then poured into ice-cooled water. The pH of the solution was adjusted to 8 with ammonium hydroxide (25%), and the aqueous phase was extracted with ethyl acetate (3×1 L). The combined organic phases were washed with brine, dried (MgSO$_4$), and the solvent was removed in vacuo (73 g). The residue was then dissolved in THF (500 ml), and to this mixture, a solution of di-tert-butyl dicarbonate (89 g) in THF (500 ml) was added. The reaction mixture was stirred at room temperature for 24 h, and the solvent was removed in vacuo. The crude product was purified on silica gel eluted with ethyl acetate-heptane (1:4) to give the title compound as an oil (92 g).

EXAMPLE 33

(+)-(1-tert-Butoxycarbonyl-2,3-dihydro-1H-indol-3-yl)acetic acid 33a (Intermediate)

Candida Antarctica Lipase (CAL, SP-435, Novo Nordisk, Denmark)(2.5 g) was suspended in (+/−)-methyl (1-tert-butoxycarbonyl-2,3-dihydro-1H-indol-3-yl)acetate 32a (50 g), and this mixture was further suspended in a 0.1 M phosphate buffer (pH=7.0) (3 L) under vigorous stirring. The reaction mixture was maintained at 25° C., and the pH was maintained at 7 by the addition of 0.5 M NaOH solution. The reaction could be monitored by the amount of added NaOH, and it was stopped after the addition of about 0.45 equivalent of base (about 120 h). The enzym was filtered of and washed with ether (1 l). The pH of the water phase was adjusted to 8. The aqueous phase was extracted with ether (2×1 l). The combined organic extracts were dried (MgSO$_4$) and evaporated to dryness in vacuo to give the starting ester enriched in a single enantiomer. The aqueous phase was cooled with ice, and the pH adjusted to 1.5 by the addition of conc. HCl. The aqueous phase was extracted with ether (3×1 l). The combined organic extracts were dried (MgSO$_4$) and the solvent was removed in vacuo to give the title compound in an enantiomeric excess of about 80–85%. Recrystallization from diisopropyl ether gave the title compound in an enantiomeric excess of 96.5%. [α]$_D$=+12.8° (c 0.45, methanol). Mp 137–138° C.

(−)-(1-tert-Butoxycarbonyl-2,3-dihydro-1H-indol-3-yl) acetic acid 33b

The enriched ester from the synthesis of 33a was treated once again as described for the racemate 32a, and the reaction mixture was worked up in a similar manner as 33a.

Ester enriched in a single enantiomer corresponding to 33.7 g was dissolved in ethanol (500 ml) and treated with 1 M NaOH solution (500 ml). The mixture was stirred at room temperature for 30 min, and the ethanol was removed in vacuo. The aqueous phase was washed with ether, cooled by the addition of ice, and the pH was adjusted to 1. The aqueous phase was extracted with ether (3×400 ml), and the combined organic extracts were washed with brine, dried (MgSO$_4$), and the solvent was removed in vacuo (31 g, enantiomeric excess of 94.6%). The residue was crystallized from diisopropyl ether (50 ml) to give the title compound in an enantiomeric excess of 97.7% (26 g). [α]$_D$=−12.6° (c=0.47, methanol). Mp 136–137° C. Chiral HPLC analysis was performed on an apparate equipped with UV detector (set at 230 nm). The analysis was performed on a on a Ultron ES OVM 150×4.6 mm, flow 1.0 ml/min, eluent 25 mM phosphate buffer (pH=4.6)/methanol/isopropanol/THF 90/5/5/0.5, T=30° C. Enantiomeric purities expressed as enantiomeric excess (ee) were calculated from peak areas.

EXAMPLE 34

(+)-(3-[1-[2-(1-Acetyl-2,3-dihydro-1H-indol-3-yl)ethyl]-1,2,3,6-tetrahydropyridin-4-yl]-6-chloro-1H-indole, 34a A mixture of (+)-(1-tert-butoxycarbonyl-2,3-dihydro-1H-indol -3-yl)acetic acid 33a (5.0 g), methanol (200 ml), and a saturated solution of HCl in ether (50 ml) was stirred at room temperature for 16 h. The solvent was removed in vacuo, and the residue was dissolved in ice-cooled water. The aqueous phase was washed with ether, and the pH was adjusted to 8 with a saturated solution of NaHCO$_3$. The aqueous phase was extracted with ethyl acetate (3×150 ml), and the combined organic extracts were washed with brine, dried (MgSO$_4$), and evaporated to dryness in vacuo (3.4 g). The residue was dissolved in THF (50 ml) and added to a suspension of LiAlH4 (1.6 g) in THF (150 ml) at about 30° C. The mixture was stirred at room temperature for 30 min and then cooled to 5° C. By drop-wise addition, water (3.2 ml), 15% NaOH solution (1.6 ml), and water (8 ml) was added. The mixture was dried (MgSO$_4$) and concentrated in vacuo. The residue was purified on silica gel eluted with ethyl acetate-ethanol (200:5) to give an oil (2.6 g). The oil was dissolved in dichloromethane (80 ml), added triethylamine (2.7 ml) and cooled to −30° C. To this mixture, a solution of acetyl chloride (1.1 ml) in dichloromethane (10 ml) was added, and the mixture was allowed to warm to 5° C. Triethylamine (2.7 ml) was added, and to this mixture, a solution of methanesulfonyl chloride (1.3 ml) in dichloromethane (10 ml) was added. The reaction mixture was purified on silica gel eluted with ethyl acetate-heptane (4:1) to give an oil (4.5 g). The oil was dissolved in methyl isobutyl ketone (100 ml) and added to a mixture of of 6-chloro-3-(1,2,3,6-tetrahydropyridin-4-yl)-1H-indole (5.5 g), K$_2$CO$_3$ (4.4 g), methyl isobutyl ketone (100 ml), and N-methylpyrrolidone (10 ml) under reflux. The mixture was boiled under reflux for 6 h and evaporated to dryness in vacuo. The residue was purified on silica gel eluted with ethyl acetate-ethanol (10:1) to give the crude product, which was recrystallized (ethyl acetate) to give the title compound (2.9 g) in an enantiomeric excess of 97.4%. [α]$_D$=+35.9° (c=0.25, methanol). Mp 169–170° C. NMR (DMSO-d$_6$) δ1.65–1.80 (m, 1H), 2.00–2.10 (m, 1H), 2.15 (s, 3H), 2.45–2.60 (m, 4H), 2.65 (broad s, 2H), 3.05–3.20 (m, 2H), 3.40–3.50 (m, 1H), 3.80 (dd, 1H), 4.25 (t, 1H), 6.10 (broad s, 1H), 6.95–7.05 (m, 2H), 7.15 (t, 1H), 7.30 (d, 1H), 7.40–7.45 (m, 2H), 7.80 (d, 1H), 8.05 (d, 1H), 11.20 (broad s, 1H). MS m/z (%): 422, 420 (MH+, 3%, 8%), 217 (30%), 174 (100%), 144 (41%).

The following compound was made in a similar manner: From 33b.

(−)-(3-[1-[2-(1-Acetyl-2,3-dihydro-1H-indol-3-yl)ethyl]-1,2,3,6-tetrahydropyridin-4-yl]-6-chloro-1H-indole, 34b.

Enantiomeric excess of 98.4%. [α]$_D$=−34.9° (c=0.27, methanol). Mp 168–169° C. Chiral HPLC analysis was performed on an apparatus equipped with UV detector (set at 230 nm). The analysis was performed on a Chiral AGP 100×4 mm, flow 0.8 ml/min, eluent 25 mM phosphate buffer (pH=6.0)/methanol/isopropanol/THF 9015/5/1, T =25° C. Enantiomeric purities expressed as enantiomeric excess (ee) were calculated from peak areas.

EXAMPLE 35

3-[1-[4-(1-Acetyl-2,3-dihydro-1H-indol-3-yl)butan-1-yl]-1,2,3,6-tetrahydropyridin-4-yl]-6-chloro-1H-indole, 35.

A mixture of 6-chloro-3-[1-[4-(2,3-dihydro-1H-indol-3-yl)butan-1-yl]-1,2,3,6-tetrahydropyridin-4-yl]-1H-indole 30b (4.9 g), triethylamine (3.7 g), and THF (200 ml) was cooled (5° C.), and the mixture was added a solution of acetyl chloride (1.0 g) in THF (50 ml). The reaction mixture was allowed to warm to room temperature, filtered and concentrated in vacuo. The residue was purified on silica gel eluted with ethyl acetate-ethanol-triethylamine (90:10:5) to give the crude product, which was recrystallized (methanol-ethyl acetate) to give the title compound (2.7 g).

$^1$H NMR (DMSO-d$_6$) δ1.30–1.45 (m, 2H), 1.45–1.60 (m, 3H), 1.75–1.85 (m, 1H), 2.15 (s, 3H), 2.40 (t, 2H), 2.45–2.55 (m, 2H), 2.55–2.65 (m, 2H), 3.10 (broad s, 2H), 3.40 (broad s, 1H), 3.70–3.80 (m, 1H), 4.20 (t, 1H), 6.10 (broad s, 1H), 6.95 (t, 1H), 7.05 (d, 1H), 7.15 (t, 1H), 7.25 (d, 1H), 7.40 (s, 2H), 7.80 (d, 1H), 8.05 (d, 1H), 11.20 (broad s, 1H). MS m/z (%): 448 (MH+, 3%), 245 (17%), 172 (100%).

EXAMPLE 36

2,3-Dimethyl-1-(2-propyl)oxybenzene, 36a (Intermediate)

To a stirred solution/suspension of 2,3-dimethylphenol (10 g) and potassium carbonate (6.8 g) in acetone (150 ml) at reflux was added 2-bromopropane (46 ml) drop-wise over 30 min. The solution was heated at reflux for 4 days. After cooling, the solvent was evaporated and the residue was dissolved in ether and water. The ether phase was separated and was worked up according to the general procedure. Column chromatography on silica gel (eluent:ethyl acetate/heptane 1:19) afforded pure 2,3-dimethyl-1-(2-propyl)oxybenzene (13.2 g) as a mobile, slightly brown oil which was used without further purification.

EXAMPLE 37

2,3-Di(bromomethyl)-1-(2-propyl)oxybenzene, 37a (Intermediate)

To a stirred solution of 2,3-dimethyl-1-(2-propyl)oxybenzene (10 g) in carbon tetrachloride (150 ml) was added N-bromosuccinimide (22 g) and dibenzoyl peroxide (370 mg) and the mixture was heated at reflux for 1.5 h. The solution was cooled to room temperature and was filtered. The residue was washed with further carbon tetrachloride (100 ml) and the combined filtrates were evaporated to give 2,3-di(bromomethyl)-1-(2-propyl)oxybenzene (21.0 g) as a yellow/orange oil which was used without further purification.

1,2-Dimethoxy-4,5-bis(chloromethyl)benzene, 37b

A stirred solution/suspension of veratrole (20 g), zinc chloride (3.2 g) and sodium chloride (420 mg) in ether (400 ml) was cooled to >20° C. using an ice-water bath, and HCl gas was bubbled through the mixture for 10 minutes. The bubbling was continued, and formaldehyde solution (26 ml, 12.3 M in water) was added dropwise over 20 minutes. Stirring/bubbling was continued for a further 4 hours, after which there was no further rise in temperature. During this time the temperature was held between 20–30° C. by the addition of ice to the cooling bath. The bubbling of HCl was then stopped, the flask was stoppered, and the mixture was stirred overnight. The solution was evaporated, and then taken up in ethyl acetate and water. The organic extractes were washed successively with sodium hydrogen carbonate solution, brine, dried over magnesium sulfate, and evaporated to yield a white/yellow solid. This was purified by column chromatography on silica gel (eluent:ethyl acetate/heptane 1:9 to 1:4) to give 1,2-dimethoxy-4,5-bis (chloromethyl)benzene (19.98 g) as a white solid, which was used without further purification.

EXAMPLE 38

Diethyl 4-(2-propyl)oxyindan-2,2-dicarboxylate, 38a (Intermediate)

Sodium hydride (7.7 g, 50–60% dispersion in oil) was rendered oil-free by washing with heptane (twice). This was then added to a solution of 2,3-di(bromomethyl)-1-(2-propyl)oxybenzene (21 g) in THF (600 ml) and the solution was heated to reflux. A solution of diethyl malonate (10.4 g) in THF (150 ml) was added drop-wise over 1 hour. After a further hour, the solution was cooled to room temperature, and water (200 ml) was added drop-wise to decompose the excess sodium hydride. The mixture was poured into aqueous hydrochloric acid (500 ml, 3 M) and was extracted with ethyl acetate (3×300 ml). The general workup procedure gave a dark oil which was purified by column chromatography on silica gel (eluent:ethyl acetate/heptane 1:9) to give diethyl 4-(2-propyl)oxyindan-2,2-dicarboxylate (11.5 g) as a clear oil, which was used without further purification.

EXAMPLE 39

4-(2-Propyl)oxyindan-2,2-dicarboxylic acid, 39a (Intermediate)

A solution/suspension of diethyl 4-(2-propyl)oxyindan-2,2-dicarboxylate (11.5 g) in potassium hydroxide solution (50 ml, 3 M) was heated at reflux for 18 hours. The solution was cooled to room temperature and was extracted with ether. The aqueous was acidified to pH<1 with aqueous hydrochloric acid (3 M) and was extracted with ethyl acetate. The standard workup afforded 4-(2 -propyl)oxyindan-2,2-dicarboxylic acid (8.5 g) as a brown solid, which was used without further purification.

EXAMPLE 40

4-(2-Propyl)oxyindan-2-carboxylic acid, 40a (Intermediate)

A solution of 4-(2-propyl)oxyindan-2,2-dicarboxylic acid (11.5 g) in NMP (20 ml) was heated to 150° C. After a further 15 minutes, the solution was allowed to cool to room temperature, and was poured into aqueous hydrochloric acid (1500 ml, 1 M). This mixture was extracted with ethyl acetate (2×500 ml) and a standard workup gave 4-(2-propyl) oxyindan-2-carboxylic acid (3.98 g) as a dark brown solid, which was used without further purification.

With compound 37b as starting material following the procedures in Examples 38, 39 and 40, the following compound was prepared:
5,6-Dimethoxyindan-2-carboxylic acid, 40b

EXAMPLE 41

6-Chloro-3-[1-[3-(2,3-dihydro-1H-indol-1-yl)-3-oxopropan-1-yl]-1,2,3,6-tetrahydropyridin-4-yl]-1H-indole 41a To a solution of indoline (6.0 g) and triethylamine (15.8 g) in THF (200 ml) was added a mixture of 3-chloropropionyl chloride (6.6 g) and THF (100 ml) at 5–9° C. The mixture was allowed to warm to room temperature, evaporated to dryness in vacuo and subjected to purification on silica gel eluted with ethyl acetate-heptane (1:2) to give a crystalline compound (5.6 g). The compound was dissolved in butanone (200 ml) and added to a boiling mixture of 6-chloro-3-(1,2,3,6-tetrahydropyridin-4-yl)-1H-indole (5.8 g), triethylamine (18.6 ml), and butanone (400 ml). The resulting mixture was boiled under reflux for 3 h, evaporated in vacuo, and the residue was purified on silica gel eluted with THF-triethylamine (95:5) to give a crystalline compound (5.4 g). The title compound was obtained after crystallization (THF-ethyl acetate-heptane).

$^1$H NMR (DMSO-$d_6$) d 2.50 (broad s, 3H), 2.65–2.85 (m, 5H), 3.05–3.20 (m, 4H), 4.15 (t, 2H), 6.10 (broad s, 1H), 6.95 (t, 1H), 7.05 (d, 1H), 7.15 (t, 1H), 7.25 (d, 1H), 7.40 (broad s, 2H), 7.80 (d, 1H), 8.10 (d, 1H), 11.20 (broad s, 1H). The following compound was made in a similar manner.
6-Chloro-3-[1-[4-(2,3-dihydro-1H-indol-1-yl)-4-oxobutan-1-yl]-1,2,3,6-tetrahydropyridin-4-yl]-1H-indole 41b. $^1$H NMR (DMSO-$d_6$) d 1.85 (t, 2H), 2.40–2.55 (m, 6H), 2.65 (t, 2H), 3.10 (broad s, 4H), 4.10 (t, 2H), 6.10 (broad s, 1H), 6.95 (t, 1H), 7.05 (d, 1H), 7.15 (t, 1H), 7.20 (d, 1H), 7.35–7.45 (m, 2H), 7.80 (d, 1H), 8.10 (d, 1H), 11.20 (broad s, 1H).

EXAMPLE 42

6-Chloro-3-[1-[3-(2,3-dihydro-1H-indol-1-yl) propan-1-yl]-1,2,3,6-tetrahydropyridin-4-yl]-1H-indole 42a The compound was prepared from 41 a as described in Example 11 but by the use of alane instead of LiAlH4 for the reduction.

$^1$H NMR (DMSO-$d_6$) d 1.75 (q, 2H), 2.40–2.60 (m, 4H), 2.65 (t, 2H), 2.90 (t, 2H), 3.00–3.20 (m, 4H), 3.25–3.40 (m. 2H), 6.10 (broad s, 1H), 6.40–6.60 (m, 2H), 6.90–7.10 (m, 3H), 7.40–7.50 (m, 2H), 7.80 (d, 1H), 11.20 (broad s, 1H).

Pharmacological Testing

The compounds of the invention were tested in well recognised and reliable methods. The tests were as follows:
$^3$H-YM-69151-2 BINDING By this method the inhibition by drugs of the binding of the dopamine $D_4$ antagonist $^3$H-YM-09151-2 to dopamine $D_4$ receptors in cloned human dopamine receptor subtype 4.2 membranes is determined in vitro. Accordingly, this is a test for affinity for dopamine $D_4$ receptors. The test is performed using a preparation of cloned dopamine $D_4$ cell membranes CRM-016®, Dupharma A/S, Denmark, in accordance with the product specifications. The results are given in the following Table 1 as $IC_{50}$-values.

TABLE 1

Binding Data (IC$_{50}$ values in nM or % inhibition of binding at 50 nM)
(* means that the test result is preliminary, nt. Means not tested)

| Comp. No. | D$_4$-bind. |
|---|---|
| 5a | 3.5 |
| 5b | 5.0 |
| 5c | 32.0 |
| 5d | 20.0 |
| 6a | 6.8 |
| 6b | 3.3 |
| 6c | 12.0 |
| 6e | 84.0 |
| 6d | 30.0 |
| 8a | 3.5 |
| 8b | 2.8 |
| 8c | 2.3 |
| 8d | 20.0* |
| 8e | 8.3 |
| 8f | 12.0 |
| 8g | 14.0 |
| 8h | 34.0 |
| 11a | 2.8 |
| 11b | 3.0 |
| 11c | 3.8 |
| 11 | 27.0 |
| 11e | 16.0 |
| 11f | 1.6 |
| 11g | 12.0 |
| 11h | 24.0 |
| 11i | 37% |
| 11j | nt. |
| 16a | 6.2 |
| 18a | 7.5 |
| 18b | 4.3 |
| 18c | 41.0 |
| 18d | 7.3 |
| 18e | 66.0 |
| 20a | 3.1 |
| 20b | 6.7 |
| 20c | 2.4 |
| 20d | 3.0 |
| 20e | 21% |
| 20f | 3.2 |
| 20g | 16.0 |
| 20h | 30.0 |
| 20i | 2.9* |
| 20j | 6.9 |
| 20k | 10.0 |
| 20l | nt. |
| 20m | 8.4 |
| 21a | 0.48 |
| 21b | 2.1 |
| 21c | 1.8 |
| 21d | 3.9 |
| 21e | 23.0 |
| 21f | 3.2 |
| 21g | 7.2 |
| 21h | 14.0 |
| 25a | 2.7 |
| 25b | 5.3 |
| 28a | 160.* |
| 28b | 14.0 |
| 28c | 13.0 |
| 29a | 6.9 |
| 29b | 2.2 |
| 30a | 9.9 |
| 30b | nt. |
| 31a | nt. |
| 34a | 4.0 |
| 34b | 24.0 |
| 35 | nt. |

$^3$H-8-OH-DPAT Binding

By this method the inhibition by drugs of the binding of the 5-HT$_{1A}$ agonist $^3$H-8-OH-DPAT (1 nM) to 5-HT$_{1A}$ receptors in membranes from rat brain minus cerebellum is determined in vitro. Accordingly, this is a test for affinity for 5-HT$_{1A}$ receptor. The test is performed as described by Hyttel et al., Drug. Dev. Res., 1988, 15, 389–404.

$^3$H-Ketanserin Binding

By this method the inhibition by drugs of the binding of $^3$H-Ketanserin (0,5 nM) to 5-HT$_{2A}$ receptors in membranes from rat is determined in vitro. The method is described in Hyttel, Pharmacology & Toxicology, 61, 126–129, 1987.

In addition to the above tests, the compounds of the invention were tested with respect to affinity for the dopamine D$_2$ receptor by determining their ability to inhibit the binding of $^3$H-spiroperidol to D$_2$ receptors by the method of Hyttel et al, J. Neurochem., 1985, 44, 1615. Furthermore, the compounds were tested with respect to their 5-HT reuptake inhibiting effect by measuring their ability to inhibit the uptake of $^3$H-serotonin into whole rat brain synaptosomes in vitro. The assay was performed as described by Hyttel, J., Psychopharmacology, 1978, 60, 13.

In general, the compounds of the invention have been found potently to inhibit the binding of tritiated YM-09151-2 to dopamine D$_4$ receptors. In addition many compounds have proven to be potent 5-HT reuptake inhibitors and many of the compounds have been found to inhibit the binding of tritiated 8-hydroxy-2-dipropylaminotetralin (8-OH-DPAT) to 5-HT$_{1A}$ receptors and/or the binding of $^3$H ketanserin to 5-HT$_{2A}$ receptors in vitro. Some compounds only bind to one of the two serotonin receptor subtypes, 5-HT$_{1A}$ or 5-HT$_{2A}$. The compounds have no substantial or only weak affinity for the dopamine D$_2$ receptor.

The VTA model is used to examine the effects on spontaneous active DA neurones in the ventral tegmental area (VTA) upon repeated oral treatment. Inhibition of the number of active DA neurones in VTA indicates an antipsychotic effect of a compound. The VTA model is described more fully in EP-A2-392 959 on page 4.

Some of the compounds of the invention has been tested and found effective in reducing the number of active DA neurons in the VTA.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders aggression, side effects induced by conventional antipsychotic agents, ischaemic disease states, migraine, senile dementia and cardiovascular disorders and in the improvement of sleep. In particular the compounds of the invention are considered useful in the treatment of positive and negative symptoms of schizophrenia without inducing extrapyramidal side effects.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc. Typical examples of recipes for the formulation of the invention are as follows:

1) Tablets containing 5.0 mg of Compound 4a calculated as the free base:

| Compound 5a | 5.0 mg |
|---|---|
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of Compound 21 calculated as the free base:

| Compound 21 | 0.5 mg |
|---|---|
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| Compound 21 | 25 mg |
|---|---|
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |

4) Solution for injection containing per milliliter:

| Compound 4a | 0.5 mg |
|---|---|
| Sorbitol | 5.1 mg |
| Acetic Acid | 0.05 mg |
| Saccharin sodium | 0.5 mg |
| Water | ad 1 ml |

What is claimed is:

1. A substituted indane or dihydroindole compound of Formula I

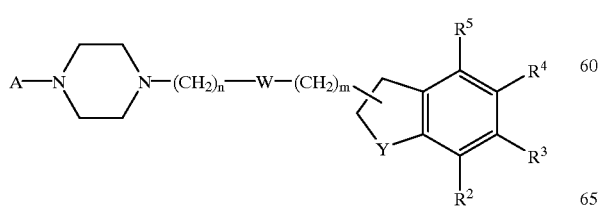

wherein A is a group

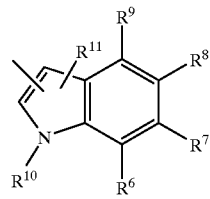

a)

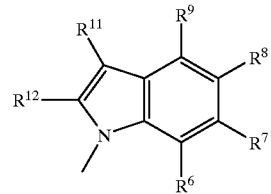

b)

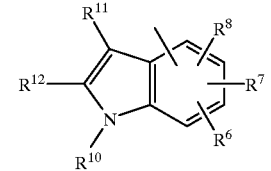

c)

Y is a hydrocarbon group completing an indane ring, a group $NR^1$ completing a dihydroindole ring, or a group N completing a dihydroindole ring linked via the 1-position;

W is a bond, and n+m is 1, 2, 3, 4, 5, or 6;

W is CO, SO, or $SO_2$, n is 2, 3, 4, or 5 and m is 0, 1, 2, or 3, provided that n+m is not more than 6; or W is O, S, n is 2, 3, 4, or 5, and m is 0, 1, 2, or 3, provided that n+m is not more than 6, and provided that if Y is N completing a dihydroindole ring attached via the 1-position then m is 2, or 3; and if Y is $NR^1$ completing a dihydroindole ring linked via the 2-position then m is 1, 2, or 3;

$R^1$ is hydrogen, $C_{1-6}$-alk(en/yn)yl, $C_{3-8}$ cycloalk(en)yl, $C_{3-8}$cycloalk(en)yl-$C_{1-6}$-alk(en/yn)yl, aryl, heteroaryl, aryl-$C_{1-6}$-alkyl, heteroaryl-$C_{1-6}$alkyl, acyl, thioacyl, $C_{1-6}$alkylsulfonyl, trifluoromethylsulfonyl, arylsulfonyl, or heteroarylsulfonyl;

$R^{15}VCO$— wherein V is O or S and $R^{15}$ is $C_{1-6}$-alk(en/yn)yl, $C_{3-8}$cycloalk(en)yl, $C_{3-8}$-cycloalk(en)yl-$C_{1-6}$-alk(en/yn)yl, aryl, or heteroaryl; or a group $R^{16}R^{17}NCO$— or $R^{16}R^{17}NCS$— wherein $R^{16}$ and $R^{17}$ are independently hydrogen, $C_{1-6}$alk(en)/yn)yl, $C_{3-8}$-cycloalk(en)yl, $C_{3-8}$-cycloalk(en)yl-$C_{1-6}$-alk(en/yn)yl, heteroaryl, or aryl, or $R^{16}$ and $R^{17}$ together with the N-atom to which they are linked, form a pyrrolidinyl, piperidinyl or perhydroazepin group; and $R^2$–$R^5$ are independently selected from hydrogen, halogen, cyano, nitro, $C_{1-6}$-alk(en/yn)yl, $C_{1-6}$ alkoxy, $C_{1-6}$-alkylthio, hydroxy, $C_{3-8}$-cycloalk(en)yl, $C_{3-8}$-cycloalk(en)yl-$C_{1-6}$-alk(en/yn)yl, $C_{1-6}$-alkylcarbonyl, phenylcarbonyl, halogen substituted phenylcarbonyl, trifluoromethyl, trifluoromethylsulfonyloxy and $C_{1-6}$ alkylsulfonyl, one of $R^2$–$R^5$ alternatively being a group —$NR^{13}R^{14}$ wherein $R^{13}$ is as defined for $R^1$ and $R^{14}$ is hydrogen, $C_{1-6}$-alk(en/yn)yl, $C_{3-8}$-cycloalk(en)yl, $C_{3-8}$-cycloalk(en)yl-$C_{1-6}$ alk(en/yn)yl, aryl, heteroaryl, aryl-$C_{1-6}$ alkyl, or heteroaryl-$C_{1-6}$-alkyl, or $R^{13}$ and $R^{14}$ together with the N-atom to which they are linked form a group

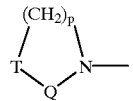

wherein

Q is C=O, C=S or $CH_2$; T is NH, N-alkyl, S, O or $CH_2$; and p is 1–4, inclusive; or two adjacent groups taken from $R^2$–$R^5$ may be joined and designate a —($CH_2$)$_3$—, or —CH=CH—NH—, thereby forming a fused 5 membered ring;

$R^6$–$R^9$ and $R^{11}$–$R^{12}$ are independently hydrogen, halogen, cyano, nitro, $C_{1-6}$-alk(en/yn)yl, $C_{1-6}$-alkoxy, $C_{1-6}$-alkylthio, hydroxy, $C_{3-8}$-cycloalk(en)yl, $C_{3-8}$-cycloalk(en)yl-$C_{1-6}$ alk(en/yn)yl, aryl, heteroaryl, phenylcarbonyl, halogen substituted phenylcarbonyl, trifluoromethyl, or $C_{1-6}$ alkylsulfonyl, or two adjacent groups taken from $R^6$–$R^9$ may together form a methylenedioxy group; $R^{10}$ is as defined for $R^1$ above;

with the proviso that the substituent $R^3$ or $R^4$ in position 6 may not be —$NR^{13}R^{14}$ when Y is $CH_2$, W is a bond, n+m is 1 and the ring is linked via the 1-position;

or a pharmaceutically acceptable acid addition salt thereof.

2. A compound of claim 1, wherein Y is $CH_2$.

3. A compound of claim 1, wherein Y is $NR^1$ or N completing a dihydroindole ring.

4. A compound of claim 3, wherein Y is $NR^1$ and that the resulting dihydroindole ring is linked to the $(CH_2)_n$—W—$(CH_2)_m$ group via the 2- or 3-position.

5. A compound of claim 3, wherein Y is N and the resulting dihydroindole is linked to the $(CH_2)_n$—W—$(CH_2)_m$ group via the 1-position.

6. A compound of claim 2, wherein A is a group a) linked a via the 2 or the 3 position, or a group b).

7. A compound of claim 6, wherein A is a group a) linked a via the 2 or the 3 position.

8. A compound of claim 2, wherein A is a group c) linked a via the 4, 5, 6, or 7 position.

9. A compound of claim 3, wherein A is a group a) linked a via the 2 or the 3 position, or a group b).

10. A compound of claim 9, wherein A is a group a) linked a via the 2 or the 3 position.

11. A compound of claim 3, wherein A is a group c) linked a via the 4, 5, 6, or 7 position.

12. A compound of claim 1, wherein Y is $NR^1$ or N completing a dihydroindole ring and A is a group a) linked a via the 2 or the 3 position.

13. A compound of claim 2, wherein the indane is linked via the 2 position and A is a group a) which is linked via position 3.

14. A compound of claim 2, wherein the indane is linked via the 2 position and A is a group a) which is linked via position 2.

15. A compound of claim 2, wherein the indane is linked via the 2 position and A is a group b).

16. A compound of claim 2, wherein the indane is linked via the 2 position and A is a group c) which is linked via position 4, 5, 6, or 7.

17. A compound of claim 2, wherein the indane is linked via the 1 position and A is a group a) which is linked via position 3.

18. A compound of claim 2, wherein the indane is linked via the 1 position and A is a group a) which is linked via position 2.

19. A compound of claim 2, wherein the indane is linked via the 1 position and A is a group b).

20. A compound of claim 2, wherein the indane is linked via the 1 position and A is a group c) which is linked via position 4, 5, 6, or 7.

21. A compound of claim 4, wherein the dihydroindole ring is linked via the 3 position and A is a group a) which is linked via position 3.

22. A compound of claim 4, wherein the dihydroindole ring is linked via the 3 position and A is a group a) which is linked via position 2.

23. A compound of claim 4, wherein the dihydroindole ring is linked via the 3 position and A is a group b).

24. A compound of claim 4, wherein the dihydroindole ring is linked via the 3 position and A is a group c) which is linked via position, 4, 5, 6, or 7.

25. A compound of claim 4, wherein the dihydroindole ring is linked via the 2 position and A is a group a) which is linked via position 3.

26. A compound of claim 4, wherein the dihydroindole ring is linked via the 2 position and A is a group a) which is linked via position 2.

27. A compound of claim 4, wherein the dihydroindole ring is linked via the 2 position and A is a group b).

28. A compound of claim 4, wherein the dihydroindole ring is linked via the 2 position and A is a group c) which is linked via position 4, 5, 6, or 7.

29. A compound of claim 5, wherein A is a group a) which is linked via position 3.

30. A compound of claim 5, wherein A is a group a) which is linked via position 2.

31. A compound of claim 5, wherein A is a group b).

32. A compound of claim 5, wherein A is a group c) which is linked via position 4, 5, 6, or 7.

33. A compound of claim 1, wherein W is a bond and m+n is 1 to 4.

34. A compound of claim 1, wherein W is a bond and m+n is 1 to 2.

35. A compound of claim 1, wherein W is a bond and m+n is 1.

36. A compound of claim 1, wherein W is a bond and m+n is 2.

37. A compound of claim 1, wherein W is a bond and m+n is 2 to 6.

38. A compound of claim 1, wherein W is a bond and m+n is 2 to 5.

39. A compound of claim 1, wherein W is a bond and m+n is 2 to 4.

40. A compound of claim 1, wherein W is a bond and m+n is 3 to 6.

41. A compound of claim 1, wherein W is a bond and m+n is 3 to 5.

42. A compound of claim 1, wherein W is a bond and m+n is 3 to 4.

43. A compound according to claim 1, wherein W is O.

44. A compound according to claim 1, wherein W is CO.

45. A compound of claim 1, wherein $R^1$ is hydrogen, $C_{1-6}$-alkyl, formyl, $C_{1-6}$-alkylcarbonyl, $C_{1-6}$-alkoxycarbonyl or $C_{1-6}$-alkylaminocarbonyl and $R^2$ to $R^5$ are independently selected from hydrogen, halogen, cyano, nitro, $C_{1-6}$-alkyl, $C_{1-6}$ alkoxy, $C_{1-6}$-alkylthio, hydroxy, $C_{3-8}$ cycloalkyl, $C_{3-8}$- cycloalkyl-$C_{1-6}$-alkyl, $C_{1-6}$-alkylcarbonyl, trifluoromethyl, trifluoromethylsulfonyloxy and $C_{1-6}$ alkylsulfonyl, one of $R^2$ to $R^5$ alternatively being a group —$NR^{13}R^{14}$ wherein $R^{13}$ is hydrogen, $C_{1-6}$-alkyl, acyl, $C_{1-2}$-alkylsulfonyl, or a group —$R^{16}R^{17}NCO$ wherein $R^{16}$ is hydrogen, $C_{1-6}$-alkyl, $C_{3-8}$-cycloalkyl, or $C_{3-8}$-cycloalkyl-$C_{1-6}$-alkyl, and $R^{17}$ is hydrogen or $C_{1-6}$-alkyl, or $R^{16}$ and $R^{17}$ together with the N-atom to which they are linked, form a pyrrolidinyl, piperidinyl, or perhydroazepin group and $R^{14}$ is hydrogen or $C_{1-6}$-alkyl, or $R^{13}$ and $R^{14}$ are linked together to form pyrrolidinyl, piperidinyl, perhydroazepin or a 5 to 7 membered unsubstituted lactam ring.

46. A compound of claim 45, wherein $R^2$ to $R^5$ is selected from hydrogen, halogen, cyano, nitro, $C_{1-6}$-alkyl, $C_{1-6}$-alkoxy, trifluoromethyl, and trifluoromethylsulfonyloxy.

47. A compound of claim 1, wherein none of $R^2$–$R^5$ is a group $NR^{13}R^{14}$.

48. A compound of claim 1, wherein at least one of $R^2$–$R^5$ is a group $NR^{13}R^{14}$.

49. A compound of claim 48 wherein $R^{13}$ is methyl, formyl, acetyl, methylaminocarbonyl, dimethylaminocarbonyl, methylsulfonyl, aminocarbonyl, cyclopropylcarbonyl, pyrrolidinylcarbonyl or 4-fluorophenylaminocarbonyl and $R^{14}$ is hydrogen or $C_{1-6}$-alkyl.

50. A compound of claim 1, wherein two adjacent groups taken from $R^2$ to $R^5$ are joined and designate —CH=CH—NH—, thereby forming a fused 5 membered ring.

51. A compound of claim 45, wherein $R^6$ to $R^9$ are independently hydrogen, halogen, cyano, nitro, $C_{1-6}$-alkyl, $C_{1-6}$-alkoxy, $C_{1-6}$-alkylthio, hydroxy, $C_{3-8}$-cycloalkyl, $C_{3-8}$-cycloalkyl-$C_{1-6}$ alkyl, trifluoromethyl, or $C_{1-6}$ alkylsulfonyl, or two adjacent groups taken from $R^6$–$R^9$ may be joined and designate a methylenedioxy group; $R^{11}$ and $R^{12}$ are hydrogen or $C_{1-6}$-alkyl, and $R^{10}$ is hydrogen, $C_{1-6}$-alkyl, or acyl.

52. A compound of claim 51 wherein $R^6$ to $R^9$ are independently selected from hydrogen, halogen, $C_{1-6}$-alkyl, $C_{1-6}$-alkoxy, or two adjacent groups taken from $R^6$–$R^9$ may be joined and designate a methylenedioxy group.

53. A compound of claim 52 wherein $R^9$ is hydrogen.

54. A compound of claim 53 wherein $R^8$ is hydrogen.

55. A compound of claim 54 wherein $R^6$ to $R^7$ are independently hydrogen or halogen.

56. A compound of claim 55 wherein $R^6$ to $R^7$ are independently hydrogen or chloro.

57. A pharmaceutical composition comprising a compound of claim 1 in a therapeutically effective amount together with one or more pharmaceutically acceptable carriers or diluents.

58. A method of treating the positive and negative symptoms of schizophrenia, other psychoses, anxiety disorders, depression, alcohol abuse, impulse control disorders, aggression, ischaemic disease states, migraine, senile dementia and cardiovascular disorders and in the improvement of sleep comprising administration of a therapeutically acceptable amount of a compound according to claim 1.

59. The method of claim 58, wherein said anxiety disorders are selected from the group consisting of generalized anxiety disorder, panic disorder and obsessive compulsive disorder.

* * * * *